US012161525B2

(12) United States Patent
Selberis et al.

(10) Patent No.: US 12,161,525 B2
(45) Date of Patent: *Dec. 10, 2024

(54) INTEGRATED DIGITAL WORKFLOW FOR PROVIDING DENTAL RESTORATION

(71) Applicant: James R. Glidewell Dental Ceramics, Inc., Newport Beach, CA (US)

(72) Inventors: Michael John Selberis, Ladera Ranch, CA (US); Sergey Vladimirovich Nikolskiy, Coto de Caza, CA (US); Shawn Andrews Ramirez, Santa Ana, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 920 days.

This patent is subject to a terminal disclaimer.

(21) Appl. No.: 17/168,892

(22) Filed: Feb. 5, 2021

(65) Prior Publication Data

US 2021/0177546 A1    Jun. 17, 2021

Related U.S. Application Data

(63) Continuation of application No. 14/625,165, filed on Feb. 18, 2015, now Pat. No. 10,912,626.

(51) Int. Cl.
A61C 7/00     (2006.01)
A61C 13/00    (2006.01)
G16H 70/20    (2018.01)

(52) U.S. Cl.
CPC .......... A61C 7/002 (2013.01); A61C 13/0004 (2013.01); G16H 70/20 (2018.01)

(58) Field of Classification Search
None
See application file for complete search history.

(56) References Cited

U.S. PATENT DOCUMENTS 7,386,797 B1    6/2008 Chatterjee et al.
8,234,143 B1    7/2012 Brewer et al.
(Continued)

FOREIGN PATENT DOCUMENTS

EP    2082556 B1    5/2013
WO    2008083857 A1    7/2008

OTHER PUBLICATIONS

USPTO Non-Final Office Action for U.S. Appl. No. 14/625,178, mailed Mar. 7, 2018, in 12 pages.
(Continued)

*Primary Examiner* — Jonathan Ng
(74) *Attorney, Agent, or Firm* — Klarquist Sparkman, LLP

(57) ABSTRACT

A computer-implemented method of routing a dental restoration design case to a user account includes receiving new dental restoration design cases associated with metadata describes design requirements. The method includes parsing the metadata to identify design factors indicating the requirements and storing the new cases in a main queue. The method also includes receiving login information, identifying the user account for the design user and retrieving attribute data associated with the account. The attribute data describes a design skill level of the design user. The method includes evaluating the design factors of the new dental restoration design cases in the main queue based on the attribute data of the account to determine a dental restoration design case in the main queue that satisfies the attribute data of the account and routing the determined dental restoration design case to a user queue associated with the user account.

19 Claims, 13 Drawing Sheets

(56) References Cited

U.S. PATENT DOCUMENTS

| | | | |
|---|---|---|---|
| 8,429,659 B2 | 4/2013 | Bartfai-Walcott et al. | |
| 8,543,234 B2 | 9/2013 | Gao | |
| 8,769,134 B2 | 7/2014 | Calder et al. | |
| 8,804,503 B2 | 8/2014 | Kalkunte et al. | |
| 8,819,701 B2 | 8/2014 | Wheeler et al. | |
| 8,838,801 B2 | 9/2014 | Alapati et al. | |
| 8,861,364 B2 | 10/2014 | Dubey | |
| 8,891,363 B2 | 11/2014 | Wu | |
| 8,891,372 B2 | 11/2014 | Garofalo et al. | |
| 8,892,740 B2 | 11/2014 | Ellis et al. | |
| 10,299,891 B2 | 5/2019 | Lemchen et al. | |
| 10,912,626 B2 | 2/2021 | Selberis et al. | |
| 2002/0018981 A1* | 2/2002 | Andersson | A61C 13/0004 |
| | | | 433/223 |
| 2002/0150859 A1 | 10/2002 | Imgrund et al. | |
| 2004/0197728 A1 | 10/2004 | Abolfathi et al. | |
| 2005/0170315 A1 | 8/2005 | Strobel et al. | |
| 2007/0038489 A1 | 2/2007 | Kayahara et al. | |
| 2007/0211081 A1 | 9/2007 | Quadling et al. | |
| 2008/0301010 A1 | 12/2008 | Klim et al. | |
| 2009/0063196 A1* | 3/2009 | Frederickson | G16H 40/20 |
| | | | 705/3 |
| 2009/0162813 A1 | 6/2009 | Glor et al. | |
| 2009/0298017 A1 | 12/2009 | Boerjes et al. | |
| 2010/0030613 A1 | 2/2010 | Williamson | |
| 2010/0174578 A1 | 7/2010 | Duffy et al. | |
| 2014/0010610 A1 | 1/2014 | Ganley et al. | |
| 2014/0136216 A1* | 5/2014 | Beebe | G06Q 40/08 |
| | | | 705/2 |
| 2014/0278279 A1 | 9/2014 | Azernikov et al. | |
| 2015/0134391 A1 | 5/2015 | Gordon et al. | |
| 2015/0317595 A1 | 11/2015 | De et al. | |
| 2017/0020638 A1* | 1/2017 | Stine | A61C 13/0006 |
| 2017/0265966 A1* | 9/2017 | Lemchen | G16H 20/00 |
| 2018/0285801 A1* | 10/2018 | Alde | G06Q 10/10 |
| 2020/0113650 A1* | 4/2020 | Lemchen | G16H 10/60 |

OTHER PUBLICATIONS

USPTO Non-Final Office Action for U.S. Appl. No. 14/625,178, mailed Mar. 29, 2019, in 16 pages.

USPTO Final Office Action for U.S. Appl. No. 14/625,178, mailed Nov. 18, 2019, in 19 pages.

USPTO Non-Final Office Action for U.S. Appl. No. 14/625,178, mailed May 15, 2020, in 14 pages.

* cited by examiner

INTEGRATED DIGITAL WORKFLOW FOR PROVIDING DENTAL RESTORATION

RELATED APPLICATION(S)

This application is a continuation patent application of U.S. application Ser. No. 14/625,165, filed Feb. 18, 2015, now U.S. Pat. No. 10,912,626, which is incorporated herein by reference in its entirety.

TECHNICAL FIELD

The disclosure relates generally to the field of dental restoration design and manufacture, and specifically to integrated digital workflow for providing dental restoration design and manufacture.

BACKGROUND

Recently, CAD/CAM dentistry (Computer-Aided Design and Computer-Aided Manufacturing in dentistry) has provided a broad range of dental restorations, including crowns, veneers, inlays and onlays, fixed bridges, dental implant restorations, and orthodontic appliances. In a typical CAD/CAM based dental procedure, a treating dentist can prepare the tooth being restored either as a crown, inlay, onlay or veneer. The prepared tooth and its surroundings are then imaged by a 3D imaging camera and uploaded to a computer. The dentist can submit the digital 3D image as an order to a dental laboratory for design and/or fabrication. Alternatively, a dentist can obtain an impression of the tooth to be restored and order from a dental laboratory for design and/or fabrication using the impression of the tooth. The impression may, alternatively, be scanned directly, or formed into a model to be scanned, and uploaded to a computer by the dentist before ordering.

When a dental laboratory receives the order for dental restoration design and/or fabrication, the dental laboratory assigns the order to a technician who can use a design station including software to design the restoration to restore the tooth to its appropriate form and function based on the requirement of the dentist. Typically, the dental laboratory assigns orders to technicians randomly or only based on availabilities of the design station or technicians. Such a system of operation has many problems, which, if unsolved, deteriorate the quality of the dental restoration design and fabrication service. For example, the system does not take into account the difference of capabilities between different technicians or design stations and also does not use the capability of the technician or design station as a factor in determining the assignment. Therefore, there can be a mismatch between the capability of the service resources and the design requirement associated with the order from the dentist. Further, when such a mismatch occurs, either human resources with high capabilities may be wasted, or low skilled human resources don't have the capability to handle the order and the order thus has to be re-assigned, causing some degree of delay for the service.

Moreover, the conventional system cannot enable a physically remote work station to participate in the order assignment among work stations to further optimize the quality of various dental restoration services. The system therefore cannot match different orders to different types of work stations either. In addition, the conventional system is not equipped with an automatic design proposal tool and therefore cannot combine the automatic design proposal tool with the order assignment scheme to achieve an even optimal operation process. Furthermore, the conventional system does not include any quality control unit to guarantee the quality of the restoration design without significantly delaying the process.

SUMMARY

A computer-implemented method of routing a dental restoration design case to a user account of a design user is disclosed. Embodiments of the method comprise receiving one or more new dental restoration design cases. Each of the new dental restoration design cases associated with metadata describes at least one requirement related to dental restoration design. The embodiments of the method also comprise parsing the metadata to identify at least one design factor indicating the at least one requirement for the each new dental restoration design case and storing the one or more new dental restoration design cases in a main queue. The embodiments of the method further comprise receiving login information from a device operated by the design user, identifying the user account for the design user based on the login information and retrieving attribute data associated with the account from a database. The attribute data describes a design skill level of the design user. The at least one design factor of the one or more new dental restoration design cases in the main queue is evaluated based on the attribute data of the account to determine a dental restoration design case in the main queue that satisfies the attribute data of the account. The determined dental restoration design case is routed to a user queue associated with the user account.

Another aspect provides a non-transitory computer-readable storage medium storing executable computer program instructions for routing a dental restoration design case to a user account of a design user. The computer-readable storage medium stores computer program instructions comprising instructions for receiving one or more new dental restoration design cases, each of the new dental restoration design cases associated with metadata describing at least one requirement related to dental restoration design, parsing the metadata to identify at least one design factor indicating the at least one requirement for the each new dental restoration design case and storing the one or more new dental restoration design cases in a main queue. The computer-readable storage medium also stores computer program instructions comprising instructions for receiving login information from a device operated by the design user, identifying the user account for the design user based on the login information, retrieving attribute data associated with the account from a database, the attribute data describing a design skill level of the design user, evaluating the at least one design factor of the one or more new dental restoration design cases in the main queue based on the attribute data of the account to determine a dental restoration design case in the main queue that satisfies the attribute data of the account, and routing the determined dental restoration design case to a user queue associated with the user account.

Another aspect provides a system for routing a dental restoration design case to a user account of a design user. One embodiment of the system has a processor and a non-transitory computer-readable storage medium comprising instructions. The instructions are executable by the processor to perform steps comprising receiving one or more new dental restoration design cases, each of the new dental restoration design cases associated with metadata describing at least one requirement related to dental restoration design, parsing the metadata to identify at least one design factor indicating the at least one requirement for the each new dental restoration design case, and storing the one or more new dental restoration design cases in a main queue. The instructions are executable to further perform steps comprising receiving login information from a device operated by the design user, identifying the user account for the design user based on the login information, retrieving attribute data associated with the account from a database, the attribute data describing a design skill level of the design user, evaluating the at least one design factor of the one or more new dental restoration design cases in the main queue based on the attribute data of the account to determine a dental restoration design case in the main queue that satisfies the attribute data of the account and routing the determined dental restoration design case to a user queue associated with the user account.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

DETAILED DESCRIPTION

Figure 1:
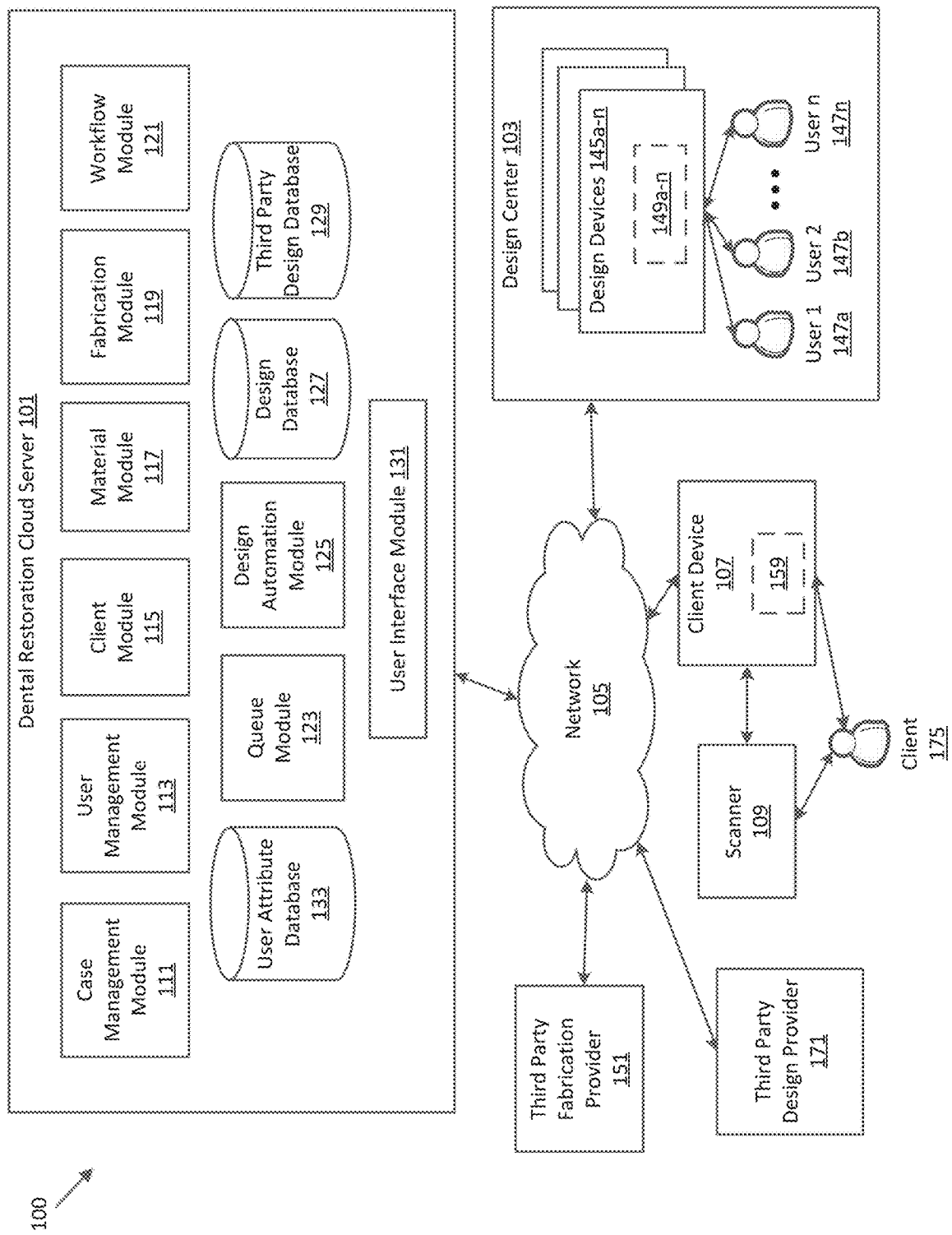
FIG. 1 is a high-level block diagram of a cloud computing environment for supporting integrated digital workflow for providing dental restoration according to one embodiment.

A dental restoration cloud system facilitating design and fabrication of dental restoration is described below. In the following description, for purposes of explanation, numerous specific details are set forth to provide a thorough understanding of the invention. However, it will be apparent to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the following detailed description are presented in terms of algorithms and symbolic representations of operations on data bits within a computer memory. These algorithmic descriptions and representations are the methods used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared or otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following disclosure, it is appreciated that throughout the disclosure terms such as "processing," "computing," "calculating," "determining," "displaying" or the like, refer to the action and processes of a computer system, or similar electronic computing device, that manipulates and transforms data represented as physical (electronic) quantities within the computer system's registers and memories into other data similarly represented as physical quantities within the computer system's memories or registers or other such information storage, transmission or display devices.

The present invention also relates to an apparatus for performing the operations herein. This apparatus may be specially constructed for the required purposes, or it may be a general-purpose computer selectively activated or reconfigured by a computer program stored in the computer. The invention may take the form of an entirely hardware embodiment, an entirely software embodiment or an embodiment including both hardware and software elements. In one embodiment, the invention is implemented in software comprising instructions or data stored on a computer-readable storage medium, which includes but is not limited to firmware, resident software, microcode or another method for storing instructions for execution by a processor.

Furthermore, the invention may take the form of a computer program product accessible from a computer-usable or computer-readable storage medium providing program code for use by, or in connection with, a computer or any instruction execution system. For the purposes of this description, a computer-usable or computer readable storage medium is any apparatus that can contain, store or transport the program for use by or in connection with the instruction execution system, apparatus or device. The computer-readable storage medium can be an electronic, magnetic, optical, electromagnetic, infrared, or semiconductor system (or apparatus or device) or a propagation medium. Examples of a tangible computer-readable storage medium include, but are not limited to, a semiconductor or solid state memory, magnetic tape, a removable computer diskette, a random access memory (RAM), a read-only memory (ROM), a rigid magnetic disk, an optical disk, an EPROM, an EEPROM, a magnetic card or an optical card, or any type of computer-readable storage medium suitable for storing electronic instructions, and each coupled to a computer system bus. Examples of optical disks include compact disk-read only memory (CD-ROM), compact disk-read/write (CD-R/W) and digital video disc (DVD).

A data processing system suitable for storing and/or executing program code includes at least one processor coupled directly or indirectly to memory elements through a system bus. The memory elements may include local memory employed during actual execution of the program code, bulk storage and cache memories providing temporary storage of at least some program code in order to reduce the number of times code must be retrieved from bulk storage during execution. In some embodiments, input/output (I/O) devices (such as keyboards, displays, pointing devices or other devices configured to receive data or to present data) are coupled to the system either directly or through intervening I/O controllers.

Network adapters may also be coupled to the data processing system to allow coupling to other data processing systems or remote printers or storage devices through intervening private or public networks. Modems, cable modem and Ethernet cards are just examples of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. It will be appreciated that a variety of programming languages may be used to implement the teachings of the invention as described herein.

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

System Overview

In this disclosure, "client" generally refers to any person or entity that may request dental restoration related services via any devices. For example, a client can be a doctor (e.g., a dentist), a hospital worker, a dental clinic, a patient, etc. "User" generally refers to a human person that provides or facilitates to provide dental restoration related services to the client. For example, a user can be a dental restoration design technician in a dental lab, a self-employed dental restoration design technician, a design quality control technician, a material technician, a milling technician, etc. The following discussion focuses on dental restoration. However, the techniques described below can also be used with other types of services.

FIG. 1 shows a cloud computing environment or system 100 for supporting integrated digital workflow for providing dental restoration design and/or fabrication according to one embodiment. The cloud computing environment 100 includes a dental restoration cloud server 101, a design center 103 including design devices 145a-n (referred to collectively or individually as design devices 145) operated by users 147a, 147b, 147n (referred to collectively or individually as users 147), a client device 107, a scanner 109, a third party fabrication provider 151 and a third party design provider 171 connected by a network 105. Only one dental restoration cloud server 101, one design center 103, one client device 107, one scanner 109, one third party fabrication provider 151 and one third party design provider 171 are shown in FIG. 1 in order to simplify and clarify the description. Embodiments of the cloud computing environment 100 can have multiple dental restoration cloud servers 101, design centers 103, client devices 170, scanners 109, third party fabrication providers 151 and third party design providers 171 connected to the network 105. Likewise, the functions performed by the various entities of FIG. 1 may differ in different embodiments.

The dental restoration cloud server 101 receives dental restoration cases from the client devices 107 operated by clients 175, manages the dental restoration cases between the different clients 175, and, in turn, provides finished dental restoration designs and/or milled dental restorations to the clients 175. In one embodiment, the dental restoration cases may include design only cases that only request the dental restoration cloud server 101 to provide a digital design of the dental restoration. In one embodiment, the dental restoration cases may request the dental restoration cloud server 101 not only to provide a design but also to fabricate the dental restoration. In one embodiment, the dental restoration cases may request fabrication only.

In order to manage dental restoration cases among different clients 175, the dental restoration cloud server 101 creates accounts for clients 175 and manages profiles for clients 175. In addition, the dental restoration cloud server 101 also creates accounts for users 147 (e.g., design technicians and quality control technicians) operating in design center 103 that design and test dental restorations using certain dental restoration design software 149a-n (referred to collectively or individually as design software 149) installed in the design devices 145, manages profiles for the users 147, and routes dental restoration cases among the users 147. Furthermore, the dental restoration cloud server 101 determines workflows of cases among different operation components according to different requirements of the cases.

In one embodiment, the dental restoration cloud server 101 includes a case management module 111, a user management module 113, a client module 115, a material module 117, a fabrication module 119, a workflow module 121, a queue module 123, a design automation module 125, a user attribute database 133, a design database 127, a third party design database 129 and a user interface module 131. Other embodiments of the dental restoration cloud server 101 include different and/or additional components. In addition, the functions may be distributed among the components in a different manner than described herein. In one embodiment, the cloud computing environment 100 may include a plurality of the dental restoration cloud servers 101 and/or other devices performing work for a plurality of requesting clients 175.

The case management module 111 receives dental restoration cases from the client device 107 operated by the client 175 (e.g., a doctor) and manages the dental restoration cases. In one embodiment, the case management module 111 obtains a dental restoration case including metadata input by a client 175. For example, the case management module 111 cooperates with the user interface module 131 to generate a user interface allowing the client 175 to enter case information and submit the case as an order. The case may request for a design and/or manufacture of a dental restoration, including, e.g., a crown, a veneer, an inlay, an onlay, a fixed bridge, a dental implant restoration, an orthodontic appliance, etc. In one embodiment, the metadata entered by the client 175 may specify one or more design or manufacture providers the client 175 desires. In one embodiment, the metadata may also indicate if the client 175 requests a restoration design only or a milled restoration, if the client 175 requests an unsintered, sintered or finished restoration, or what type of shade the client 175 desires, etc.

In one embodiment, the client 175 may also add one or more time requirements associated with the case. For example, the client 175 requires the case to be finished within a certain period of time, e.g., one hour, two hours, five hours, 12 hours, 24 hours, one week, etc. In other examples, the client 175 may input special dimensional or quality requirement of the restoration for specific patients.

In one embodiment, the case management module 111 parses the metadata associated with the dental restoration case and validates the dental restoration case based on the parsed metadata. If the dental restoration case is not valid, the case management module 111 cooperates with the user interface module 131 to notify the client 175. For example, an error message can be generated and sent to the client device 107 of the client 175. Other examples of notification may include communicating the error message to the client 175 through the client's account, email or phone. Once the dental restoration case submitted by the client 175 is validated, an internal "case in progress" message can be transmitted from the case management module 111 to other appropriate modules, e.g., the workflow module 121, or the queue module 123, etc., to route the case to one or more of the design center 103 or a third party design provider 171 and/or a third party fabrication provider 151 for processing.

In one embodiment, the case management module 111 also parses the metadata associated with the case requesting a dental restoration design and identifies one or more design factors related to dental restoration design accordingly. Each design factor indicates one requirement related to dental restoration design specified by the client 175. For example, a design factor indicates a dental restoration type, i.e., if the dental restoration is a crown, a veneer, an inlay, an onlay, a fixed bridge, a dental implant restoration or an orthodontic appliance, etc. Other examples of the design factor can include, but are not limited to, a time requirement (e.g., one hour, two hours, 24 hours, etc.), design quality requirement, dimensional design requirement, etc. Those of skill in the art may recognize that additional examples of the design factor are also possible.

In one embodiment, the case management module 111 further tags the dental restoration case with the identified design factors and categorizes the dental restoration case accordingly. For example, the case management module 111 tags cases with the corresponding dental restoration types and categorizes the cases according to the dental restoration types. In one embodiment, these functions of identifying one or more design factors, tagging cases with the design factors and categorizing the cases may be performed by other appropriate modules, e.g., the workflow module 121 or the queue module 123.

The user management module 113 creates user accounts for users 147 based on user information input by the users 147. In one embodiment, the user management module 113 may receive information from an administrator and creates an administrator account accordingly. In one embodiment, the user management module 113 is initiated by an administrator to invite other users 147 to enter their information for creating their user accounts. For example, the user management module 113 cooperates with the user interface module 131 to send an invitation and display an information entering page on a device (e.g., a smart phone, a tablet, a notebook, a desktop computer, etc.) operated by a user 147. The information entering page allows the user 147 to input user information for creating a user account and in one embodiment also requires the user 147 to sign an agreement for creating the user account.

The user information can include, but is not limited to, a user name or identifier (ID), an email address, a password, security questions and answers, an icon, etc. Other examples of the user information may also be recognized by those of skill in the art. In one embodiment, the user 147 may be required by the user management module 113 to enter work related information including, e.g., a work experience, an education background, a certificate, an award, a recommendation, a professional title, a length of work, brief work self-description, etc. This type of information may be used to evaluate a skill level of the user 147 and the skill level of the user 147 may be advantageously used for routing suitable cases to the user 147 for design. The skill level can be attached to the user account of the user 147. Accordingly, wherever users 147 are (e.g., the users 147 can all be remotely located), by their user accounts, suitable dental restoration design cases can be routed to them.

Once the user 147 has entered the user information and clicks to sign the agreement, the user management module 113 may validate the user information and signature for the agreement. The user management module 113 may create a user account and/or generate a user profile based on the user information. Furthermore, the user management module 113 may manage the user account for the user 147 by updating the account information or user profile based upon the user's request. As long as the user account is active, when the user 147 logs in the account via any device (e.g., a design device 145 or any other device such as a smart phone, a tablet or a PC), the user management module 113 receives login information and identifies the user account based on the login information. In one embodiment, upon the user's login, the user management module 113 cooperates with the user interface module 131 to display a user page showing dental restoration design cases that the user 147 has designed, the user 147 is working on at that moment or are available for the user 147 to design.

In addition, in some embodiment, upon the established user account the user management module 113 may also authorize the user 147 to download the dental restoration design software 149 on the design devices 145 to design dental restorations. In one embodiment, the user management module 113 also establishes a hierarchical group structure among the user accounts based on their profiles. For example, the user management module 113 determines groups and sub-groups and assigns user accounts to corresponding groups or sub-groups. A group or sub-group may represent a design center 103 or a third party design provider 171.

In one embodiment, the user management module 113 may cooperate with an embedded program or module (not shown in FIGS) to determine attribute data of the user 147 based on the user information or the user's 147 profile. For example, the user management module 113 triggers the program to assess a skill level or score of the user 147 using the user information. In another embodiment, the user management module 113 may transfer part or all of the user information to a third party server (not shown in the FIGS) to evaluate the user's skill level or score. The user management module 113 may receive attribute data indicating a skill level or score from the third party evaluation server. The attribute data of a user 147 may alternatively describe a comprehensive work ability of the user 147. For example, the comprehensive work ability of the user 147 includes, but is not limited to, work efficiency, work quality, a work qualification, management capability of the user 147. Those of skill in the art can recognize that other types of attribute data may be possible. In one embodiment, the user management module 113 associates the attribute data with the user's 147 account and stores the attribute data in the user attribute database 133. In addition, the user management module 113 may receive updated user information and update the user account profile as well as the attribute data in the database 133 accordingly.

In one embodiment, the user management module 113 determines a role for a user account based on its attribute data. For example, the user management module 113 determines whether a user 147 is qualified to be a design technician, a supervisory design technician, or a quality control (QC) technician, etc., based upon the attribute data of the user's account. If a user 147 is qualified to be a QC technician, the user management module 113 assigns a QC role to the user's account. If a user 147 is qualified as a design technician, the user management module 113 assigns a designer role to the user's account. The user attribute database 133 stores the user accounts including user profiles of the users 147. In addition, the user attribute database 133 also stores attribute data and user roles associated with the user accounts.

The client module 115 manages clients 175 as well as the relations between the clients 175. For example, the client module 115 can set up an account and a profile for a client (e.g., a doctor) 175. The client module 115 can store the account and the profile for the client 175 in a database (not shown in FIGS) for further search, edit or delete. In one embodiment, the client module 115 can also classify the doctors to different practices. For example, a doctor 175 can belong to several practices and a practice may contain several doctors 175. In one embodiment, with the established account and profile, the client 175 is allowed to submit cases or other requests to the dental restoration cloud server 101.

The material module 117 manages material parameters used for designing and/or milling the dental restorations. For example, the material module 117 sets up the default values for the material parameters included in the software used for dental restoration design. In one embodiment, the material module 117 may adjust the values of the material parameters for different clients 175 based upon their requests.

The fabrication module 119 enables the fabrication of the dental restorations based on designs. For example, the fabrication module 119 receives a digital design file describing a dental restoration design from a design center 103, a client device 107 (e.g., the client 175 designs the dental restoration by self), or a third party design provider 171. Based on the digital design file, the fabrication module 119 generates a milling tool path to be followed by a milling tool to remove margin material from a work piece to create the designed dental restoration.

The workflow module 121 is triggered by receiving a new dental restoration case from the case management module 111 and transfers the case to appropriate design center 103 or providers 171, 151 to process the case according to the requirement related to the case. In one embodiment, the workflow module 121 stores the new dental restoration case in a main queue once it is received. In one embodiment, the workflow module 121 determines whether the dental restoration case requests design or fabrication. If the case requests design, the workflow module 121 routes the case to the design database 127 for the design center 103 to design or a third party design database 129 for the third party design provider 171 to design according to designation of the client 175. If the case includes a completed design (e.g., a digital design file) of the restoration (e.g., done by either the client 175 self or a third party design provider 171) and only requests fabrication of the design, the workflow module 121 transfers the case to the fabrication module 119 for milling the restoration.

In one embodiment, the workflow module 121 sends cases requesting for design to queue module 123 for routing the design cases to specific user accounts of the users 147 based on certain criteria. For example, the queue module 123 routes received new dental restoration design cases by evaluating design factors of the design cases based on attributes of the users 147 that are able to perform the design. In one embodiment, the queue module 123 also routes dental restoration design cases based upon quality control (QC) test results. The queue module 123 will be described in more detail below with reference to FIG. 2. The attribute-based routing of design cases can beneficially achieve the match between a design case and a design technician, therefore achieving the most efficient resource-task assignment.

The design database 127 stores a main queue including dental restoration design cases, e.g., available dental restoration design cases for design users 147 to design, rejected design cases by quality control (QC) users 147, etc., that are requested by one or more clients 175 to be designed by the dental restoration cloud server 101. In one embodiment, the main queue may also include dental restoration cases in which impressions are received and need to be scanned for obtaining digital scanned model of the teeth. The main queue may include information indicating the status of the cases. For example, the status of the cases include, but is not limited to, scanning (e.g., the case is being scanned at the moment or has been sent to a user 147 for scanning by the moment), scan completed (e.g., the case has been scanned or the user 147 scanning it has uploaded a digital scanned model to the system), designing (e.g., the case has been routed or assigned to a design user 147 by the moment), design completed (e.g., the case has been designed and/or approved by quality control user 147), fabricating (e.g., the case is being fabricated at the moment or the design of the case has been passed on to a fabrication module 119 or provider 151), fabrication completed (e.g., the case has been fabricated), outsourced (e.g., the case has been sent to a third-party design/fabrication provider 151, 171), etc. In one embodiment, the design database 127 may also stores individual user queues for the design users 147 and/or QC users 147. Alternatively, the user queues are included in the main queue. For example, a user queue is a subsection of the main queue. The third party design database 129 stores dental restoration design cases requested by one or more clients 175 to be designed by the third party design provider 171.

The design automation module 125 enables pre-processing for qualified dental restoration design cases. For example, once receiving a new dental restoration case for design from the case management module 111, the design automation module 125 may filter a new dental restoration design case based on its design factors to determine whether the design case is qualified for pre-processing. An example for a qualified dental restoration design case may be a single unit, posterior design. Additional examples for a qualified design case may include, but be not limited to, a bridge design, multiple unit posterior design, anterior design, etc. Those of skill in the art may recognize other types of example for qualified design case are possible. This functionality may alternatively implemented by the queue module 123 in other embodiments.

If the design case is qualified for pre-processing, the design automation module 125 pre-processes the design case (e.g., processes the design case before a user 147 starts to design the case) to determine a design proposal. For example, the design automation module 125 performs an automatic feature detection on the scanned model, an automatic arc fitting to detected features, an automatic scaling of the library arch form to the scanned model, an automatic rigid and/or non-rigid registration of the library arch and the scanned model, and restoration design proposal, as described in patent application Ser. No. 14/468,946, filed on Aug. 26, 2014, which is hereby incorporated herein by reference in its entirety.

The user interface module 131 cooperates with one or more other components of the dental restoration could server 101 to provide user interfaces (UIs) to clients 175 or users 147. For example, the user interface module 131 receives instructions from the case management module 111 to generate user interface data for displaying a user interface that allows a client 175 to input case information and submit the case as an order. In another example, the user interface module 131 receives instructions from the user management module 113 to generate data for showing an invitation and a user interface that allows a user 147 to accept the invitation and input user information to register a user account. Those of skill in the art may recognize other functions of the user interface module 131 may be possible.

The network 150 enables communications among the dental restoration cloud server 101, the design center 103, the client device 107, the third party fabrication provider 151 and the third party design provider 171. In one embodiment, the network 150 uses standard communications technologies and/or protocols. In another embodiment, the entities can use custom and/or dedicated data communications technologies instead of, or in addition to, the ones described above. For example, the network 105 may be a conventional type of network, wired or wireless, and may have any number of configurations such as a star configuration, token ring configuration or other configurations known to one skilled in the related art. In one embodiment, the network 105 comprises one or more of a local area network (LAN), a wide area network (WAN) (e.g., the Internet), and/or any other interconnected data path across which multiple devices communicate. In another embodiment, the network 105 is a peer-to-peer network. The network 105 is coupled to or includes portions of a telecommunications network for sending data in a variety of different communication protocols. For example, the network 105 is a 3G network or a 4G network. In yet another embodiment, the network 105 includes Bluetooth communication networks or a cellular communications network for sending and receiving data such as via short messaging service (SMS), multimedia messaging service (MMS), hypertext transfer protocol (HTTP), direct data connection, Wireless application protocol (WAP), email, etc. In yet another embodiment, all or some of the links in the network 105 are encrypted using conventional encryption technologies such as secure sockets layer (SSL), secure HTTP and/or virtual private networks (VPNs).

A client device 107 is an electronic device used by a client 175 to perform functions such as receiving and/or reviewing scanned dental models from the scanner 109 designing the dental restorations based on the scanned dental models using the dental restoration design software 159, submitting new dental restoration cases to the dental restoration cloud server 101 for design and/or fabrication, or receiving finished dental restoration from the dental restoration cloud server 101 through the network 105. For example, the client device 107 may be a smart phone, or a tablet, notebook, or desktop computer. The client device 107 includes and/or interfaces with a display device on which the client 175 may view the scanned dental models or completed dental restoration design. In addition, the client device 107 provides a user interface (UI), such as physical and/or on-screen buttons, with which the client 175 may interact with the client device 107 to perform functions such as submitting a new dental restoration case, designing a dental restoration, receiving and review a completed dental restoration design, etc.

The design center 103 may include one or more servers or design devices 145 interacted by one or more users 147 to facilitate the accomplishment of the dental restoration design cases submitted by the clients 175. In one embodiment, a design device 145 may be a smart phone, or a tablet, notebook, or desktop computer. A design software 149 used for digital design of the dental restoration can be installed in the design device 145. The users 147 may use the design software 149 to design the dental restoration. In one embodiment, a user 147 may alternatively operate on another device (e.g., a smart phone, a tablet, a notebook or a desktop computer) to register a user account with the dental restoration cloud server 101.

In one embodiment, the design center 103 receives dental restoration design cases routed by the queue module 123 via the network 105 and sends back the finished dental restoration design to the cloud server 101. In one embodiment, the design center 103 may return rejected dental restoration designs to the dental restoration cloud server 101 for re-routing and re-design. In one embodiment, the system 100 includes multiple design centers 103 classified based upon physical locations. In another embodiment, the multiple design centers 103 included in the system 100 may be classified based on skill levels or comprehensive abilities of the users 147 associated with each design center 103.

The scanner 109 may be any type of device for scanning a prepared tooth and its surroundings or a dental impression. The scanner 109 can generate a digital file of the scanned tooth and its surroundings or a teeth impression, and transmit the file to the client device 107. As described above, the file can be used by the client 175 to create and send a dental restoration case to the dental restoration cloud server 101 for design and/or fabrication. In an alternative example, the client 175 can use the file to design the dental restoration on the client device 107 by own.

The third party design provider 171 may be any one or more servers or devices providing dental restoration designs to the dental restoration cloud server 101 through the network 105. In one embodiment, the third party design provider 171 may be required to sign an agreement with the dental restoration cloud server 101. In one embodiment, the third party design provider 171 includes devices equipped with the same or different design software from the software 149 installed in design devices 145.

The third party fabrication provider 151 may be any one or more devices providing fabrication of the dental restoration. For example, the third party fabrication provider 151 may receive finished dental restoration design files from the dental restoration cloud server 101 and instructs a milling tool to fabricate the dental restorations based on the design files. Similarly, in one embodiment, the third party fabrication provider 151 may be required to sign an agreement with the dental restoration cloud server 101.

Example Queue Module 123

Figure 2:
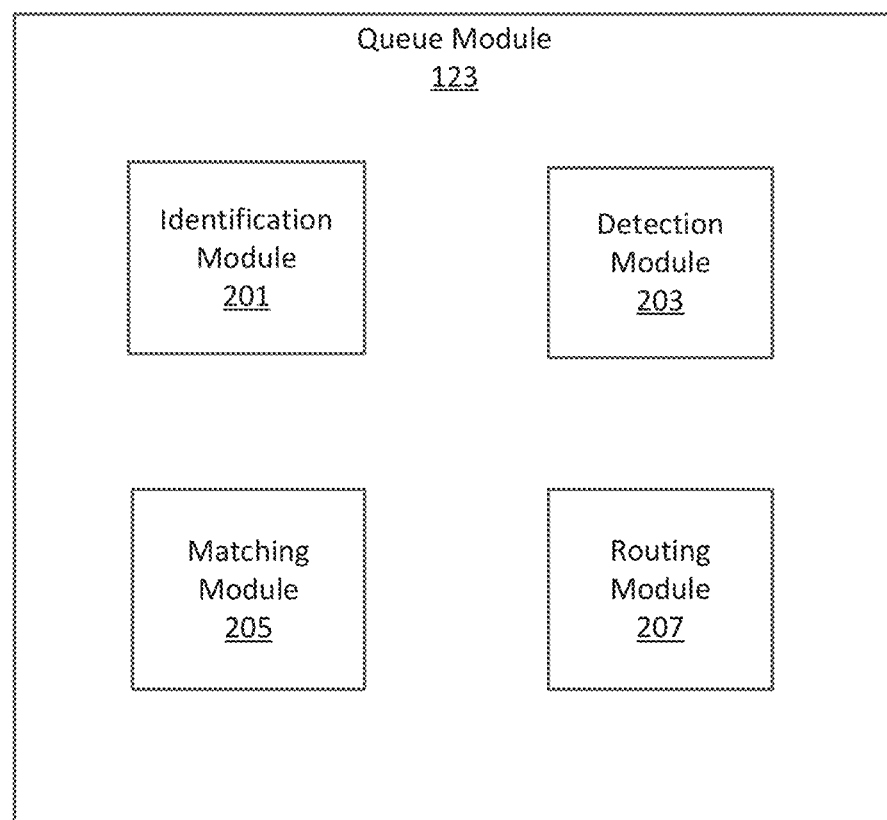
FIG. 2 is a high-level block diagram illustrating a queue module according to one embodiment.

FIG. 2 is a high-level block diagram illustrating a queue module 123 for supporting skill-based routing of dental restoration cases according to one embodiment. In the embodiment shown, the queue module 123 includes an identification module 201, a detection module 203, a matching module 205 and a routing module 207. Those of skill in the art will recognize that other embodiments of the queue module 123 can have different and/or additional modules other than the ones described here, and that the functions may be distributed among the modules in a different manner.

The identification module 201 identifies design factors related to new dental restoration design cases. In one embodiment, the identification module 201 receives new dental restoration design cases from the case management module 111 or the workflow module 121. For example, a dental restoration design case may include a 3D image of a prepared tooth to be restored and its soundings. In another example, the dental restoration design case may include a scanned file of a tooth impression. In yet another example, the client 175 may send an impression of a patient's teeth with the new dental restoration case and an administrator or a technician operating on the dental restoration cloud server 101 can scan the impression and upload the scanned tooth impression to the dental restoration cloud server 101. The identification module 201 receives the dental restoration design case and the attached image of teeth or scanned dental model of impression from the workflow module 121.

In one embodiment, the new dental restoration design case may also include metadata describing case information that includes one or more requirements related to dental restoration design of the case. The identification module 201 parses the metadata associated with the new dental restoration design case to identify one or more design factors indicating the one or more requirements related to dental restoration design. In one embodiment, the design factor may specify a dental restoration type. For example, the design factor indicates that the case is a crown restoration design, a veneer restoration design, or a bridge restoration design. Other dental restoration types may include, but not be limited to, an inlay restoration design, an onlay restoration design, a dental implant restoration design and an orthodontic appliance design, etc. In one embodiment, the design factor may specify a time requirement to complete the dental restoration design. For example, the design factor may indicate the dental restoration design case is requested to be completely designed within one hour. Other range of time limitation may also possible, such as two hours, 12 hours, 24 hours, one week, etc. In one embodiment, the design factor may specify a certain quality requirement (e.g., the quality of the design is requested to satisfy a certain criterion, etc.). In other embodiments, the design factor may specify a dimensional or size requirement for design, or any other kind of requirements known by those of skill in the art.

In one embodiment, the identification module 201 associates the identified design factors with the dental restoration design case and stores the design case and its associated design factors in the main queue in the design database 127. The identification module 201 may tag the dental restoration design case with the identified design factor. In addition, the identification module 201 may categorize the dental restoration design case according to the design factor. For example, the identification module 201 categorizes the crown design cases into one group, and the bridge design case into another group, etc. In another example, the identification module 201 groups the dental restoration design cases based on their time urgency (e.g., a group for one hour design cases, a group for 24 hour design cases, a group for one week design cases, etc.).

The identification module 201 may be an optional component of the queue module 123. Accordingly, in one embodiment the above functions may be performed by the case management module 111 or workflow module 121 and the queue module 123 may receive outputs (e.g., the identified design factors associated with dental restoration design cases) from the case management module 111 or the workflow module 121.

The detection module 203 detects a trigger event for routing the dental restoration design cases to user accounts for design. In one embodiment, the detection module 203 detects if a user 147 has requested a next dental restoration design case. For example, when a user 147 logs in via a device, the user management module 113 receives login information and identifies the user's account based on the login information. A user page may be generated upon the identification of the user account and displayed on the device of the user 147. The user page may include one or more dental restoration design cases that the user 147 has already designed, the user 147 is working on at the moment or are available for the user 147 to work on. In addition, the user page allows the user 147 to request one or more dental restoration design cases to work on. For example, the user page includes a "Get next" button that is clickable for the user 147 to request a next dental restoration design case. Once the user 147 clicks the "Get next" button, the detection module 203 detects that the user 147 has requested a next dental restoration design case and receive a request indicating it from the device (e.g., a design device, or any other devices such as a smart phone, a tablet, etc.) operated by the user 147. The user page will be described in further detail below with reference to FIG. 9.

The detection module 203 may, in one embodiment, monitor the number of the dental restoration design cases available for the user 147 to design and determine whether the available dental restoration design cases are less than a certain amount. For example, the detection module 203 detects whether the number of the available dental restoration design cases has fallen below a threshold, e.g., 10, five, one. If the detection module 203 detects that the number is below the threshold, the detection module 203 informs the user account that the number is below the threshold and suggests the user account to request one or more new dental restoration design cases. For example, the detection module 203 may cooperate with the user interface module 131 to generate and display an alert message to the user account or a user page to show the number of the available cases in a highlighted manner. The user 147 may request a next dental restoration design case through the user account. Upon the request, the user 147 can work on the next dental restoration design case in the user queue through the user account.

Once the detection module 203 receives the request for a next dental restoration design case, the detection module 203 passes the request on to the matching module 205. Upon receiving the request, the matching module 205 retrieves attribute data associated with the user's account from the user attribute database 133. For example, the matching module 205 may query the user attribute database 133 using the user account information (such as a user ID) and obtain the attribute data associated with the user account.

Further, the matching module 205 evaluates new dental restoration design cases stored in the main queue in the design database 127. For example, the matching module 205 evaluates the one or more design factors associated with each of the new dental restoration design cases in the main queue. The matching module 205 may evaluate the design factors based on attribute data of the user account to determine a new dental restoration design case that has one or more design factors satisfying the attribute data of the user account. For example, the attribute data of a user account indicates an entry level of crown restoration design (e.g., less than three years of experience in doing crown restoration design) of the user account. The matching module 205 may use the entry level of crown design to evaluate the design factors of the new dental restoration cases to be designed to determine if there is a case having one or more design factors matching the entry level of crown design. For example, the matching module 205 may identify from the new dental restoration design cases a case requiring a single crown design within a week and without any special quality or dimensional requirement.

In another example, the attribute data of a user account may indicate a senior level (e.g., more than five years of experience) of a more complex restoration design (e.g., a bridge design). Accordingly, the matching module 205 may determine dental restoration design cases, from simple, non-urgent cases without special quality requirement to complex, urgent cases with high quality requirement, all matching the senior level of complex restoration design. The matching module 205 may, therefore, identify more matching cases in the main queue for the senior level use account than the entry level user account. The matching module 205 may generate a list of the matching cases' identifiers and send the list to the routing module 207. Alternatively, the matching module 205 may also rank the matching cases based on how closely the case matches the attribute data of the user account. For example, a case with design factors indicating a simple crown design without any special quality requirement may be ranked lower than a case with design factors indicating a complex bridge design with high quality requirement, although both the cases match the senior level of the user account. In this way, when routing a case to the user account for design, best task-resource matching can be achieved. Accordingly, with a limited amount of resources, the system can accomplish as most as possible and as hardest as possible tasks. That is, if a user account is qualified to do a certain difficulty level task, assigning the user account the most matching task will not waste the human and computer resource.

In addition, in one embodiment, the matching module 205 may also check the role of the user account and evaluate design factors of the new dental restoration design cases to determine a case satisfying the role of the user account. For example, if the user account has a quality control (QC) role, the matching module 205 may evaluate the design factors of the design cases to identify the cases to be tested for quality control for this user account. If the user account has a design role only, the matching module 205 may evaluate the design factors and identify the cases to be designed for the user account. Further, if the user account is qualified for both design and QC role, the matching module 205 can determine both cases to be designed and to be tested for QC match the user account's role. In such a scenario, the matching module 205 may rank the cases to be tested for QC higher than the cases to be designed, or vice versa depending on certain pre-determined criteria by the administrator of the system. Similarly, by prioritizing the cases based upon the user account's role, better operation efficiency may be achieved.

The routing module 207 routes the new dental restoration design cases to user queues associated with user accounts. In one embodiment, the routing module 207 receives data from the matching module 205 indicating the one or more matching dental restoration design cases for a user account. The routing module 207 determines one case from the matching cases and routes the case to a user queue associated with the user account. For example, the routing module 207 receives a list of ranked new dental restoration design cases that match the attribute data of the user account in different degrees. The routing module 207 routes the highest ranked case from the main queue to the user queue of the user account.

Once the user 147 has finished a dental restoration design case in the user queue of the user account, the routing module 207 routes the finished case to a QC user queue of a QC user account for quality control test. In one embodiment, the routing module 207 may detect that a QC user 147 has rejected the design of the dental restoration design case finished by the design user 147. Additionally, the routing module 207 also receives the rejected design annotated with rejection reasons. The rejection reasons are annotated by the QC user 147 testing the design based upon certain criteria regarding, e.g., occlusion, contact, etc. For example, the certain criteria may form a standard operating procedure (SOP). If the QC user 147 decides that the design has a deviation from the SOP, the QC user 147 may annotate the design with rejection reasons specifying design errors or other inappropriate issues of the design deviating from the SOP.

In one embodiment, the design software 149 provides certain pre-defined rejection reasons for the QC users 147 to select. Example of the pre-defined rejection reasons used by a QC user 147 may include, but not be limited to, high or low occlusion, mesial contact open or tight, distal contract open or tight, prescription from the client such as a doctor 175 (Rx) not followed, minimum thickness violation, open margin line, over or under contoured, poor anatomy, central dissectional grooves misaligned, occlusion table too wide or too narrow, marginal ridge too low or too high, emergence profile under or over contoured. Those of skill in the art can recognize any additional examples of rejection reasons for rejecting the design of the dental restoration. The QC user 147 may select one or more reasons from the above pre-defined rejection reasons via a dropdown menu.

In addition, the rejected design may also be annotated with graphs (such as drawings of the QC user 147) specifying where the error or issue takes place, and/or texts describing the rejection reasons. For example, the QC user 147 can click on the design and draw an arrow or any other appropriate shapes or graphs to show where the error or issue is. The QC user 147 can also add a comment describing the error or issue to where the error or issue is on the design. The rejected design annotated with rejection reasons and comments will be described in more detail with reference to FIG. 10.

Upon receiving the rejected design of the case, the routing module 207 detects whether the user 147 that has designed the case is available. For example, the routing module 207 detects if the user 147 logs in with the user account and/or the user account is active (e.g., not being idle, etc.) at the moment. If so, the routing module 207 routes the rejected design case back to the user queue for the user 147. The routing module 207 may place the rejected design case on top of all other cases in the user queue. In this way, the rejected design case can have a higher priority than all other cases in the user queue and the user 147 is enabled to view and handle the rejected design case right away or right after the accomplishment of the case that the user 147 is currently working on. Once the user 147 fixes the problems of the rejected design, the routing module 207 routes the fixed design back to the QC user queue of the QC user 147 for quality control examination again. The process can repeat until the case passes the test for quality control and is approved by the QC user 147. At that point, the routing module 207 may send the completed and approved design case to an appropriate module for the next processing, e.g., to the fabrication module 119 for milling the dental restoration based upon the design, or to the case management module 111 for transmitting the design to the third party fabrication provider 151 designated by the client 175 for milling or to the client device 107 for further processing by the client 175, etc.

In one scenario, the user 147 that has designed the rejected case is not available at the time of rejection. For example, the user 147 has logged out or has been idle for a certain period of time when the routing module 207 is about to route the rejected case. In such a scenario, the routing module 207 routes the rejected case back to the main queue and places the rejected case on top of all other cases in the main queue. Thus, the rejected case can be routed to a next available user 147 with the highest priority. For example, when the next user 147 requests a next design case, the routing module 207 may route the rejected case to the user 147 as long as the rejected case matches the attributes of the user 147. Similarly, after the rejected case is fixed, it can be sent back to a QC user queue for a QC user 147 to do the quality control exam again. The QC user 147 can be the same as or different from the previous QC user 147 who has done the QC test. Until the design case passes the QC test, the process can keep running recursively.

In one embodiment, the routing module 207 may monitor a user account's status to detect if an event has occurred based on the user account's status. For example, the routing module 207 determines if the user 147 is being actively logged in with the user account, if the user 147 has logged out of the user account, or if the user 147 has been idle for a certain period of time even when being logged in with the account. The Event may be that the user 147 has logged out of the user account, or that the user has been idle for a certain period of time (e.g., for one hour, for two hours, for 12 hours, for 24 hours, etc.). Other types of events indicating that the user 147 is inactive with the user account may also be recognized by those of skill in the art. Once the routing module 207 detects that such an event has occurred, e.g., the user 147 has logged out of the user account, the routing module 207 may identify dental restoration design cases in the user queue associated with the user account and return the identified cases to the main queue. Accordingly, responsive to another user 147 (e.g., a user 147 is being actively logged in with the user account) requesting a next design case, the routing module 207 can re-route the returned case from the main queue to the requesting user's queue.

Computing System Architecture

The entities shown in FIG. 1 are implemented using one or more computers.

Figure 3:
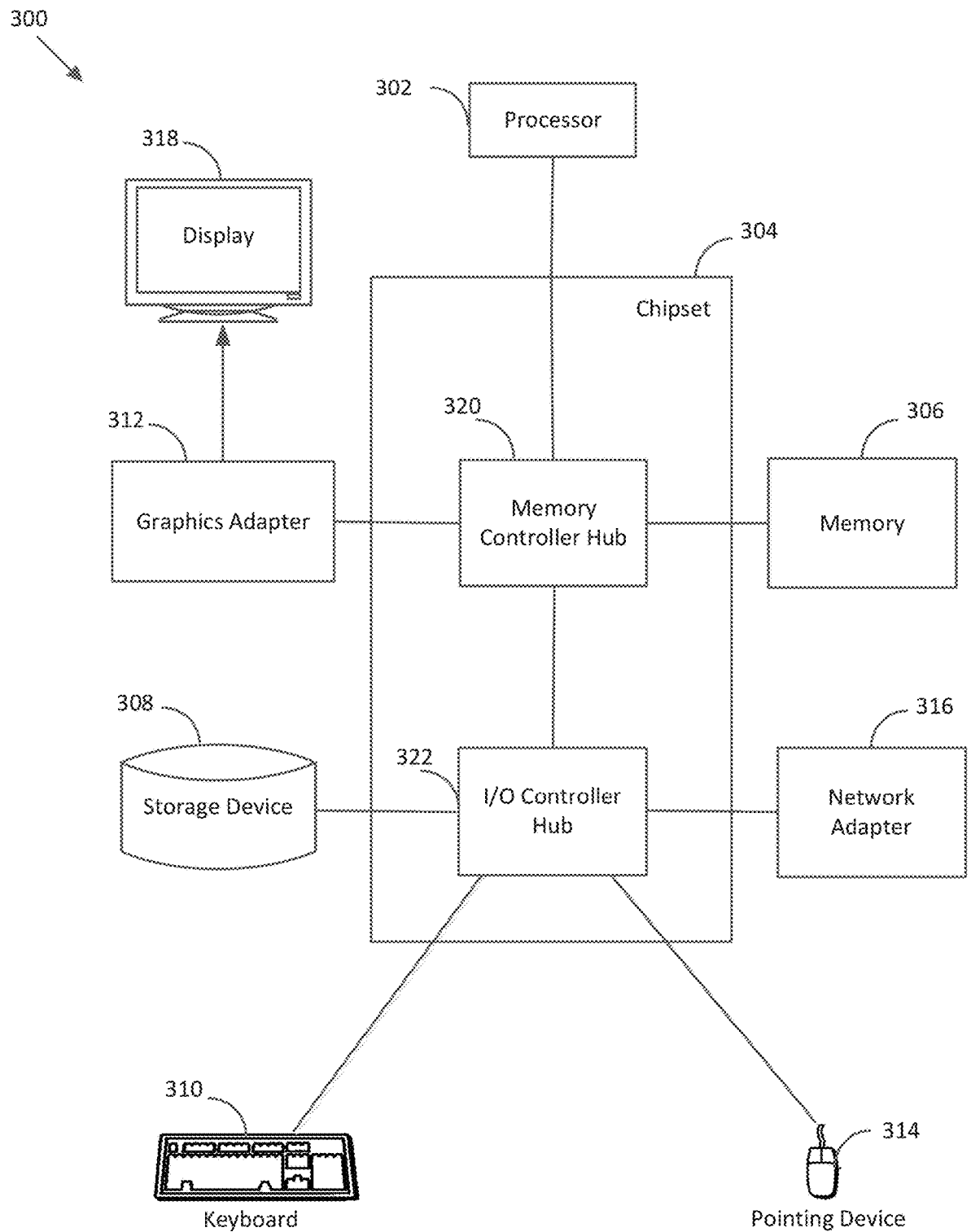
FIG. 3 is a high-level block diagram illustrating an example of a computer for acting as a cloud server, a client device, a design device, and/or any of the providers in one embodiment.

FIG. 3 is a high-level block diagram of a computer 300 for acting as a component of the dental restoration cloud server 101, a design device 145, a third party design provider 171, a component of a third party fabrication provider 151 and/or a client device 107. Illustrated are at least one processor 302 coupled to a chipset 304. Also coupled to the chipset 304 are a memory 306, a storage device 308, a keyboard 310, a graphics adapter 312, a pointing device 314, and a network adapter 316. A display 318 is coupled to the graphics adapter 312. In one embodiment, the functionality of the chipset 304 is provided by a memory controller hub 320 and an I/O controller hub 322. In another embodiment, the memory 306 is coupled directly to the processor 302 instead of the chipset 304.

The storage device 308 is any non-transitory computer-readable storage medium, such as a hard drive, compact disk read-only memory (CD-ROM), DVD, or a solid-state memory device. The memory 306 holds instructions and data used by the processor 302. The pointing device 314 may be a mouse, track ball, or other type of pointing device, and is used in combination with the keyboard 310 to input data into the computer system 300. The graphics adapter 312 displays images and other information on the display 318. The network adapter 316 couples the computer system 300 to the network 150.

As is known in the art, a computer 300 can have different and/or other components than those shown in FIG. 3. In addition, the computer 300 can lack certain illustrated components. For example, the computers acting as the store server 110 can be formed of multiple blade servers linked together into one or more distributed systems and lack components such as keyboards and displays. Moreover, the storage device 308 can be local and/or remote from the computer 300 (such as embodied within a storage area network (SAN)).

As is known in the art, the computer 300 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 308, loaded into the memory 306, and executed by the processor 302.

Exemplary Methods

Figure 4:
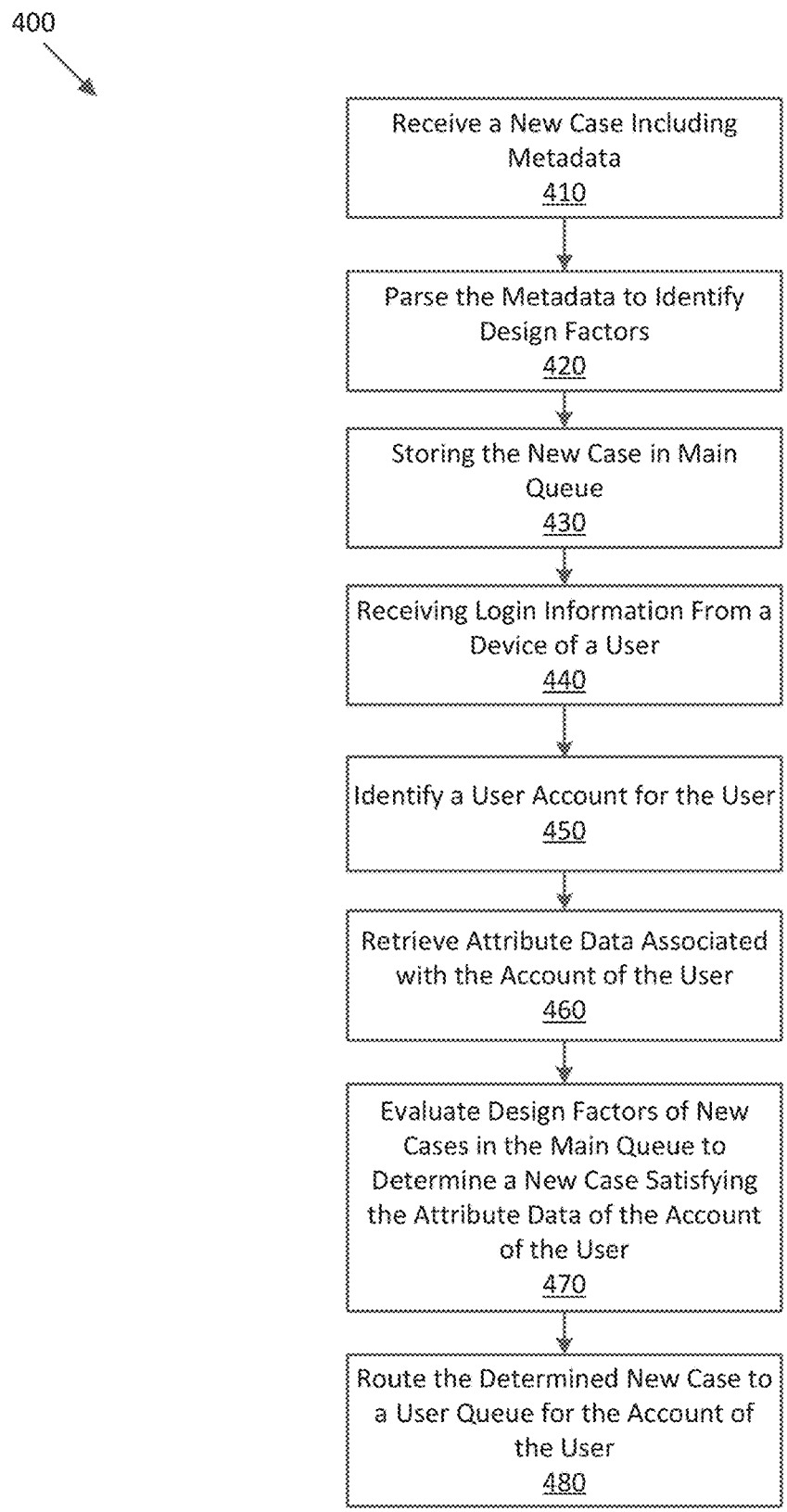
FIG. 4 is a flowchart illustrating a process for routing a new dental restoration case to a user account according to one embodiment.

FIG. 4 is a flowchart illustrating a process 400 for routing a new dental restoration design case to a user account according to one embodiment. FIG. 4 attributes the steps of the process to the queue module 123 and the user management module 113. However, some or all of the steps may be performed by other entities such as the case management module 111 and/or the workflow module 121. In addition, some embodiments may perform the steps in parallel, perform the steps in different orders, or perform different steps.

Initially, the queue module 123 receives 410 a new dental restoration design case including metadata from the workflow module 121. For example, the case management module 111 receives a dental restoration case attached with a 3D image of a prepared tooth and its surroundings or a dental impression scanned file from a client device 107 of a client 175 such as a doctor. In another example, the case management module 111 may receive the case attached with an impression of the patent's teeth from the client 175. An administrator or a technician can scan the impression and attach the scan file to the case. The case management module 111 sends the case and the attachment to the workflow module 121 to route the case to next step. If the workflow module 121 determines that the case is requesting a restoration design, the workflow module 121 sends the case to the queue module 123 for routing the design case.

In one embodiment, the queue module 123 parses 420 the metadata to identify one or more design factors. For example, the design factor may indicate a dental restoration type. In other examples, the design factor may include a time requirement, a design quality requirement, or a dimensional requirement, etc. The queue module 123 may further categorize the dental restoration design case based on its design factors. The queue module 123 stores 430 the new dental restoration design case in the mail queue for design and a following quality control test.

The user management module 113 receives 440 login information from a device operated by a user 147. For example, a user 147 (e.g., a design technician) submits login information for login via a design device 145. The user management module 113 identifies 450 a user account for the user 147 based on the login information.

In one embodiment, the user 147 may request to work on a next dental restoration design case. The queue module 123 may receive the request from the design device 145 through the network 105. The queue module 123 retrieves 460 attribute data associated with the user account of the user 147 from the user attribute database 133.

The queue module 123 evaluates 470 the design factors of the new dental restoration design cases in the main queue to determine a new case that has design factors satisfying the attribute data of the user account. For example, if the attribute data of the user account indicates that the user 147 has a junior level of crown design, the queue module 123 may determine a new design case requiring a single unit crown design without special quality requirement for the user account. The queue module 123 routes 480 the determined new case to a user queue for the user account of the user 147.

FIGS. 5A-5D are flowcharts illustrating a process 500 for routing a new dental restoration design case to a user account according to another embodiment. FIGS. 5A-5D attribute the steps of the process to the user management module 113, the case management module 111, the queue module 123 and the design automation module 125. However, some or all of the steps may be performed by other entities such as the workflow module 121. In addition, some embodiments may perform the steps in parallel, perform the steps in different orders, or perform different steps.

Figure 5A:
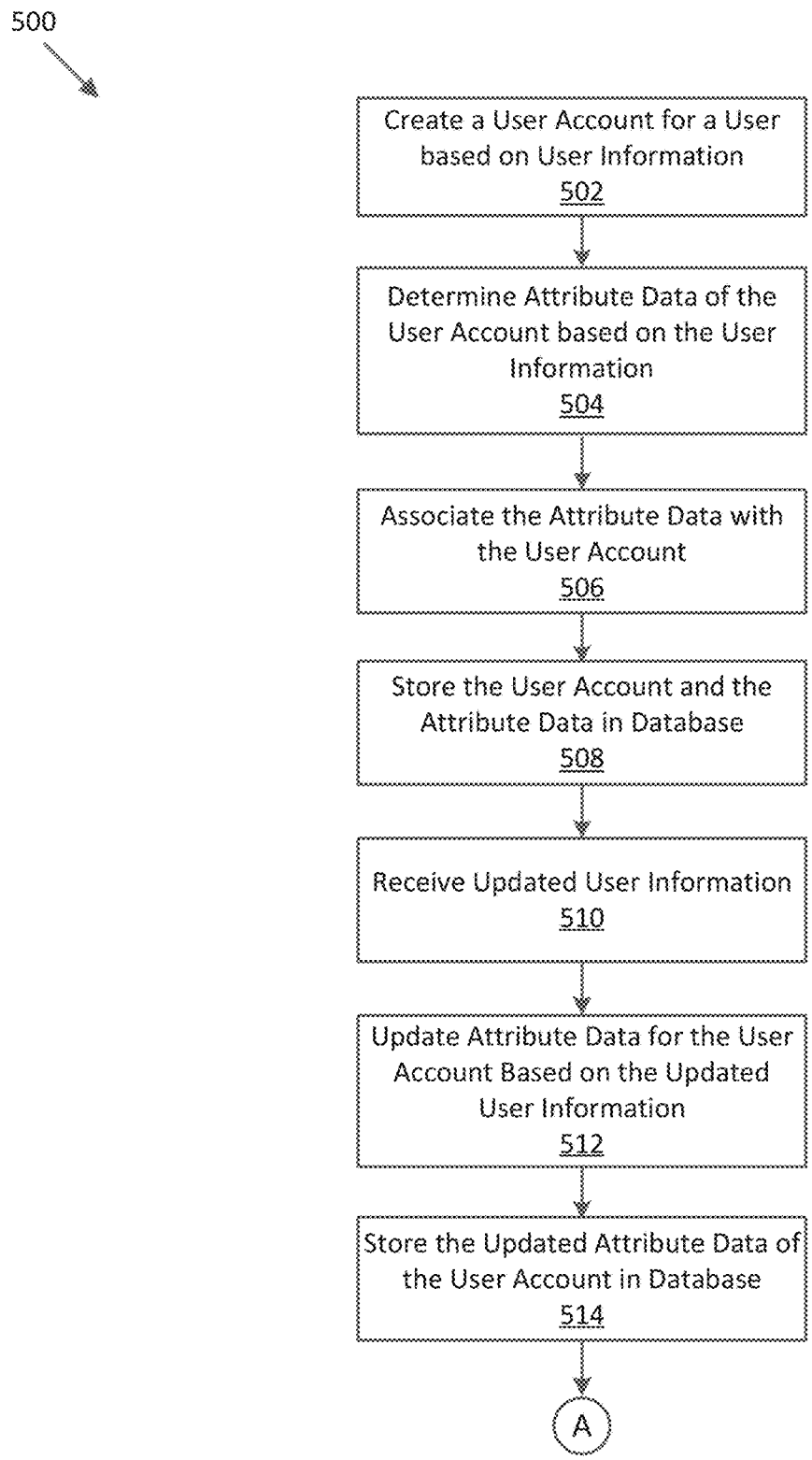
FIGS. 5A-5D are flowcharts illustrating a process for routing new dental restoration cases to a user according to another embodiment.

As depicted in FIG. 5A, the user management module 113 creates 502 a user account for a user 147 based on user information. For example, the administrator who has an administrator account with the system may send an invitation to a user 147 to invite the user to register an account with the system. Upon receiving the invitation, the user 147 may accept the invitation and input user information. In addition, the user 147 may also be required to sign an agreement. Upon the user 147 signing the agreement, the user management module 113 creates a user account for the user 147 based on the user information.

The user management module 113 determines 504 attribute data of the user account based on the user information. For example, the user management module 113 calls a program to calculate comprehensive design ability score or estimate a design skill level of the user account based on the user information. In another example, the user management module 113 may transmit the user information to a third party evaluation server to perform the evaluation and receive the resulting ability score or skill level from the third party server. The user management module 113 associates 506 the attribute data with the user account. Further, the user management module 113 stores 508 the attribute data associated with the user account in the user attribute database 133.

At step 510, the user management module 113 receives updated user information of the user account. The user management module 113 updates 512 the attribute data for the user account based on the updated user information and stores 514 the updated attribute data of the user account in the user attribute database 133.

Figure 5B:
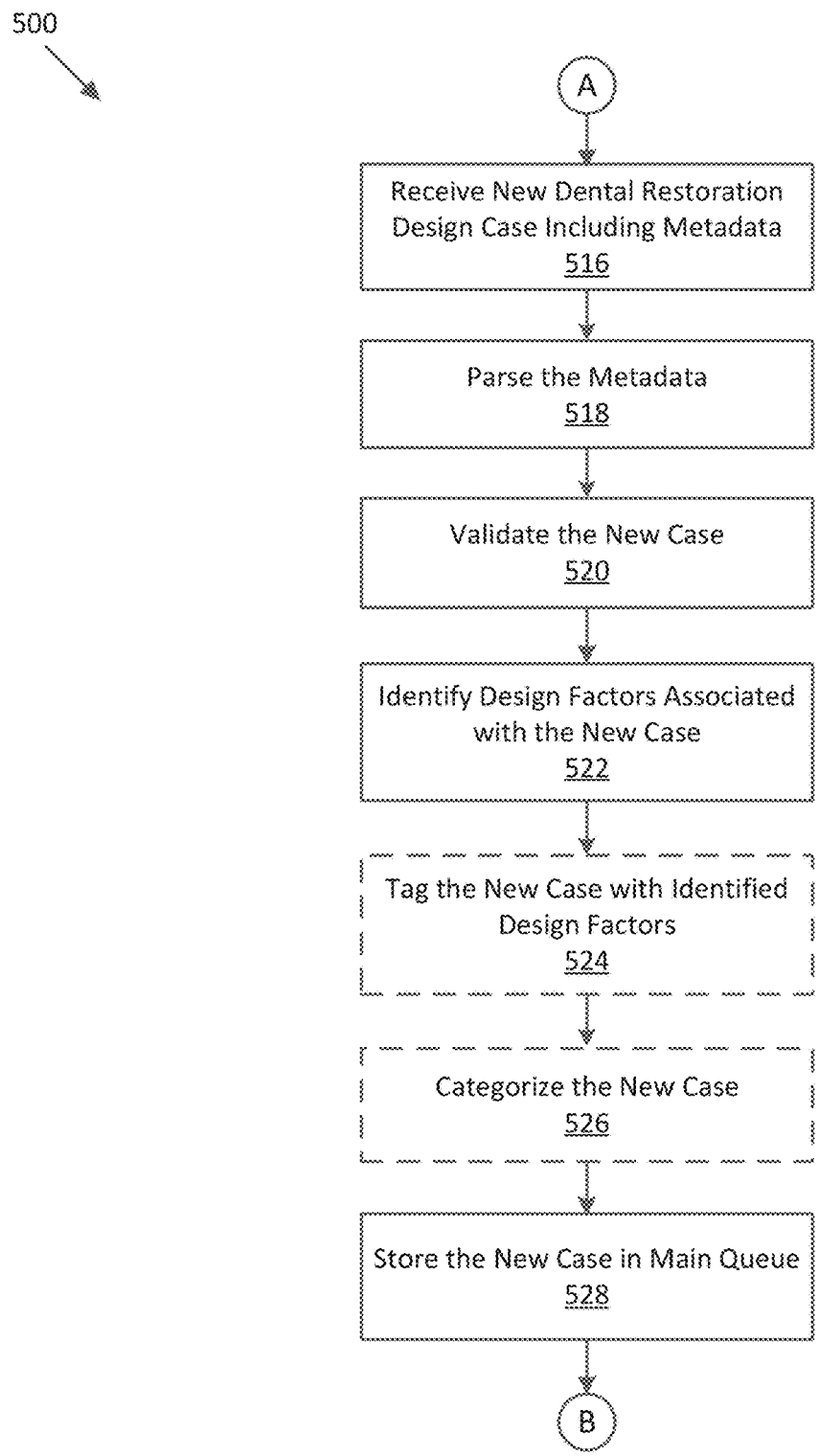

Turning to FIG. 5B, at step 516, the case management module 111 receives new dental restoration design cases including metadata. The case management module 111 parses 518 the metadata and validates 520 the new dental restoration design case based on the metadata. The case management module 111 identifies 522 design factors associated with the new dental restoration design case based on the parsed metadata. Alternatively, the queue module 123 or the workflow module 121 may perform some or all of the steps 518, 520, 522. Optionally, the queue module 123 or the workflow module 121 tags 524 the new case with the identified design factors and categorizes 526 the new case based on the design factors. The queue module 123 or the workflow module 121 stores 528 the new case in a main queue in the design database 127.

Figure 5C:
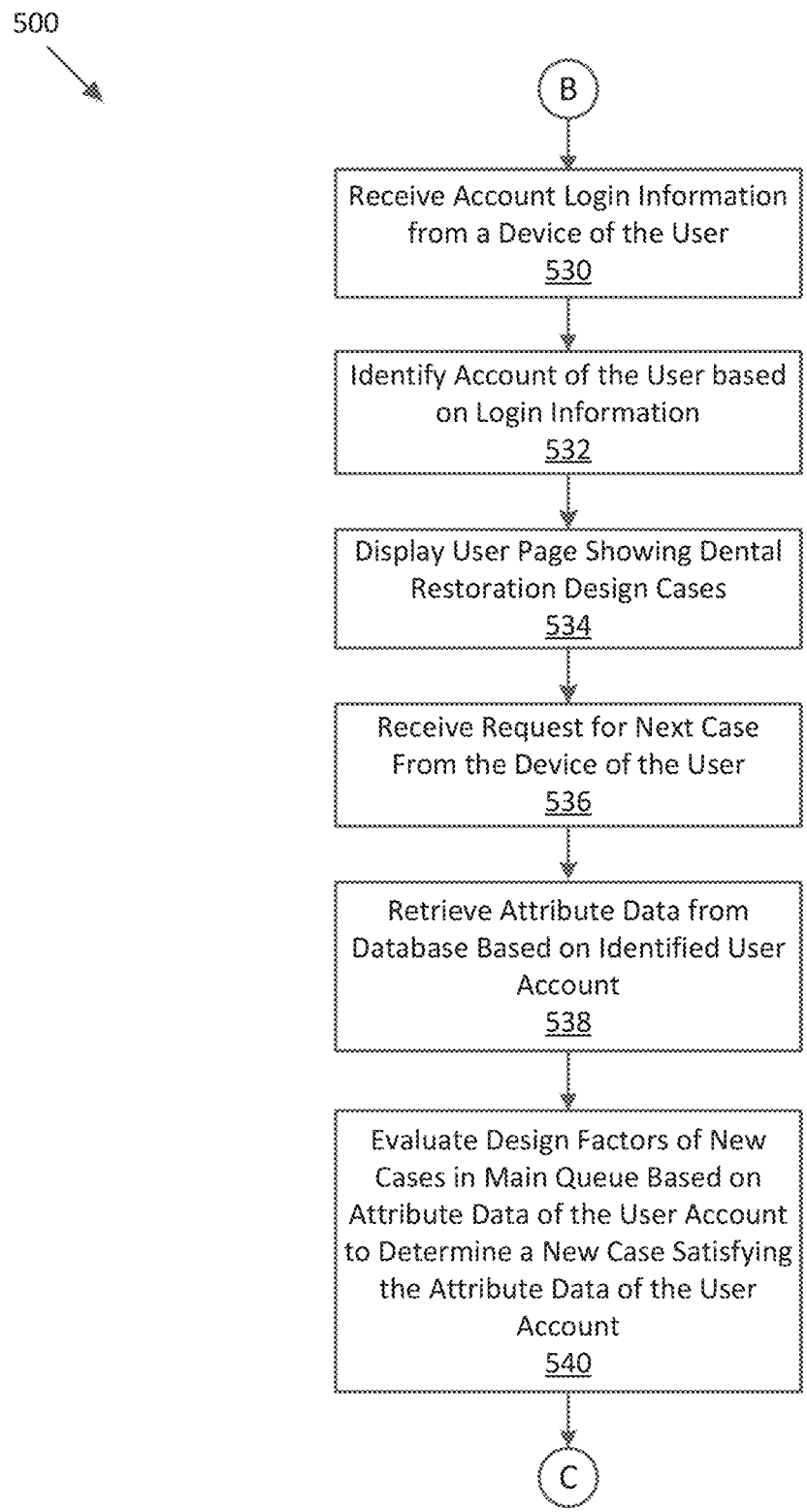

Referring now to FIG. 5C, the user management module 113 receives 530 account login information from a device (e.g., a design device 145, or any other device such as a smart phone, a tablet, etc.) of the user 147. The user management module 113 identifies 532 the user account of the user 147 based on the login information. In one embodiment, the user management module 113 cooperates with the user interface module 131 and displays 534 a user page showing dental restoration design cases for the user account. The user management module 113 receives 536 a request for a next dental restoration design case from the device of the user 147 and passes on the request to the queue module 123.

At step 538, the queue module 123 retrieves attribute data from the user attribute database 133 based on the identified user account. The queue module 123 evaluates 540 design factors of the new cases in the main queue based on the attribute data of the user account to determine a new case satisfying the attribute data of the user account.

Figure 5D:
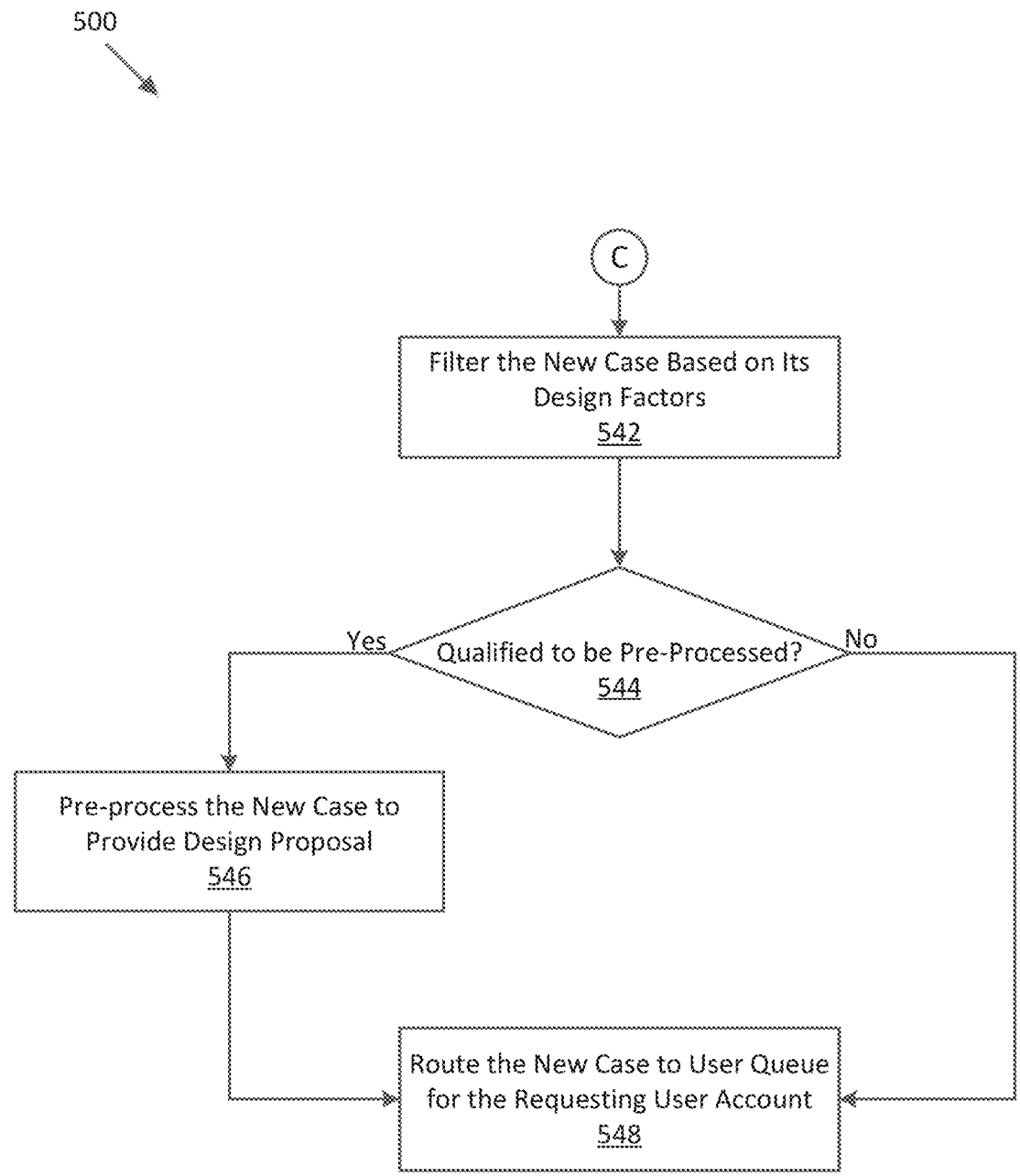

Turning to FIG. 5D, at step 542, the design automation module 125 filters the new dental restoration design case based on its design factors to check if the new case is qualified to be pre-processed. The design automation module 125 determines 544 whether the new design case is qualified to be pre-processed. If the design automation module 125 determines that the new design case is qualified for pre-processing, the design automation module 125 pre-processes 546 the new case to provide a dental restoration design proposal. At step 548, the queue module 123 routes the new case (and the design proposal if there is any) to a user queue for the requesting user account. In this way, with a design proposal, the human design time can be dramatically reduced. Furthermore, the pre-processing is performed during the user 147 is working on other design cases, which allows a further improvement of operation efficiency.

Figure 6:
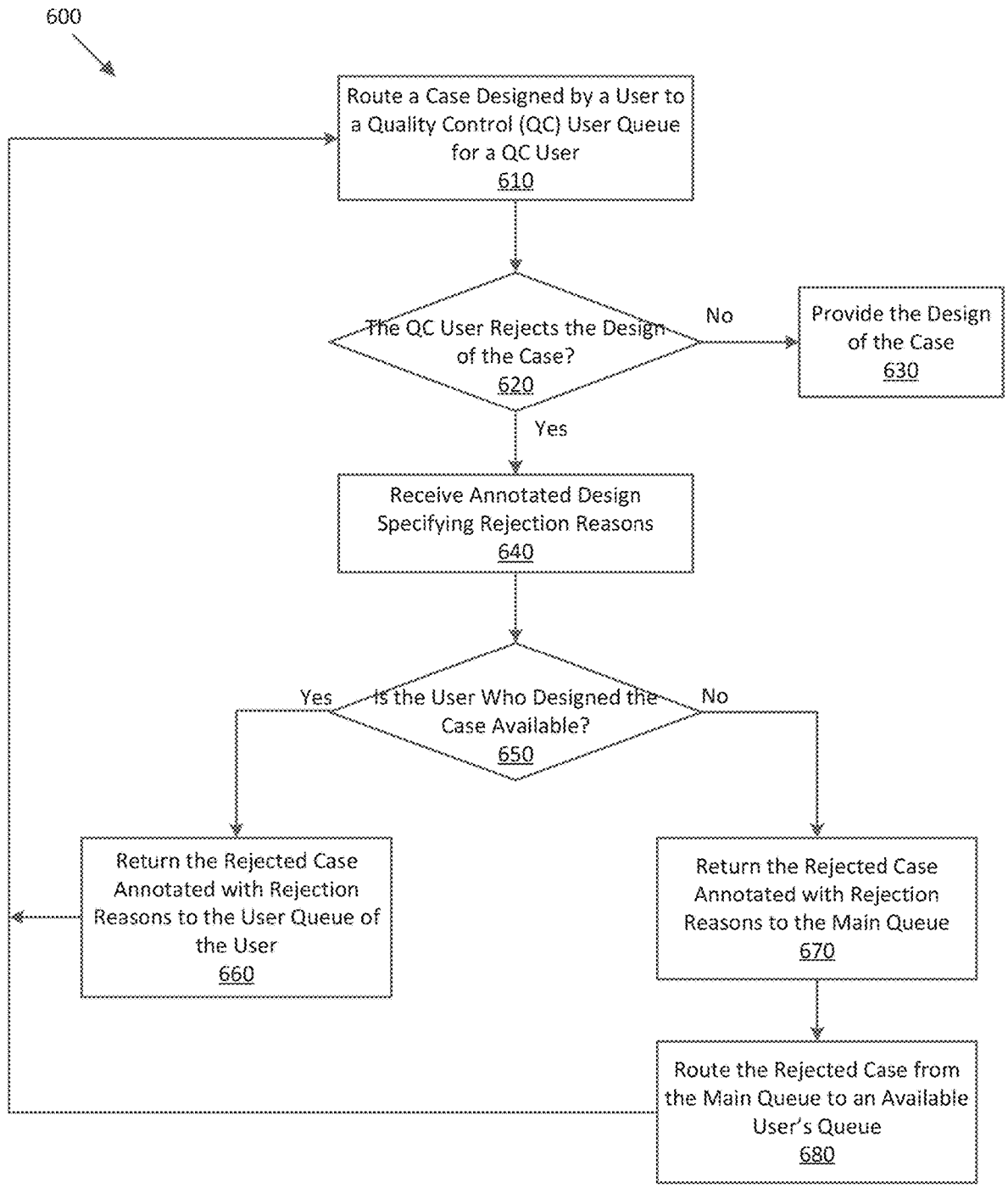
FIG. 6 is a flowchart illustrating a process for routing dental restoration cases based on quality control result according to one embodiment.

FIG. 6 is a flowchart illustrating a process 600 for routing dental restoration cases based on quality control result according to one embodiment. FIG. 6 attributes the steps of the process to the queue module 123. However, some or all of the steps may be performed by other entities. In addition, some embodiments may perform the steps in parallel, perform the steps in different orders, or perform different steps.

The queue module 123 routes 610 a case designed by a user to a quality control (QC) user queue for a QC user 147. The queue module 123 detects 620 whether the QC user 147 rejects the design of the case. If the queue module 123 detects that the QC user 147 does not rejects the design of the case and has approved the design of the case, the queue module 123 provides 630 the design of the case to other appropriate modules for next processing according to requirement of the client 175. For example, the queue module 123 sends the approved design of the case to the fabrication module 119 for milling the dental restoration based on the design.

If the queue module 123 detects that the QC user 147 rejects the design of the case, the queue module 123 receives annotated design specifying one or more rejection reasons from the QC user account. For example, the queue module 123 receives the design annotated by the QC user 147 with design errors or other inappropriate issues of the design. The queue module 123 determines 650 whether the user 147 who designed the case is available. For example, the queue module 123 detects if the user 147 has been actively logged in with the user account. If the user 147 is available, the queue module 123 returns 660 the rejected case annotated with rejection reasons to the user queue of the user 147 for fixing the problem. If the user 147 is not available, the queue module 123 returns 670 the rejected case annotated with rejection reasons to the main queue and routes 680 the rejected case from the main queue to an available user's queue once the available user 147 requests a next case via the user account.

Figure 7:
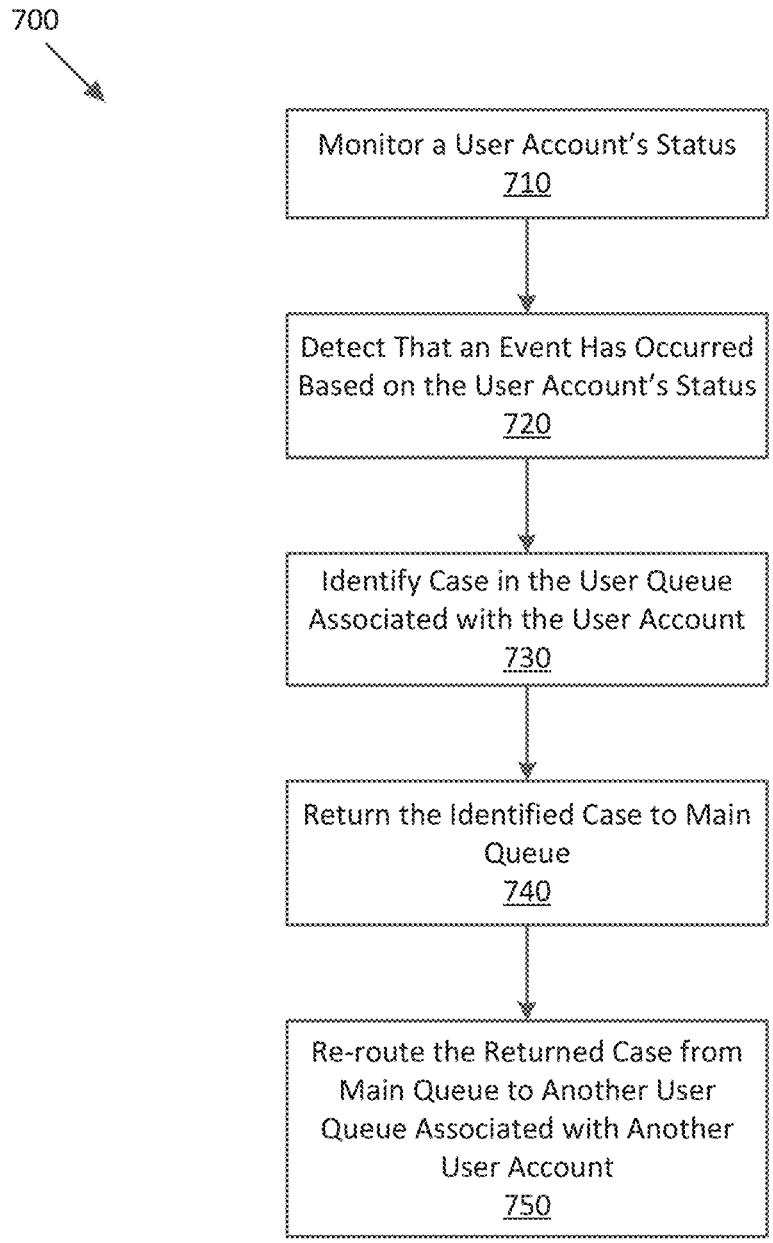
FIG. 7 is a flowchart illustrating a process for re-routing dental restoration cases based on user account's status according to one embodiment.

FIG. 7 is a flowchart illustrating a process 700 for re-routing dental restoration cases based on user account's status according to one embodiment. FIG. 7 attributes the steps of the process to the queue module 123. However, some or all of the steps may be performed by other entities. In addition, some embodiments may perform the steps in parallel, perform the steps in different orders, or perform different steps.

The queue module 123 monitors 710 a user account's status and detects if an event has occurred based on the user account's status. For example, the event may be that the user 147 has logged out of the user account, or that the user 147 has been idle for a certain period of time although being logged in with the user account. At step 720, the queue module 123 detects that the event has occurred. The queue module 123 identifies 730 dental restoration design cases in the user queue associated with the user account. The queue module 123 returns 740 the identified cases to the main queue. The queue module 123 re-routes 750 the returned cases from the main queue to another user queue associated with another user account once the other user 147 requests a next case via the user account.

Exemplary Graphical User Interfaces

Figure 8:
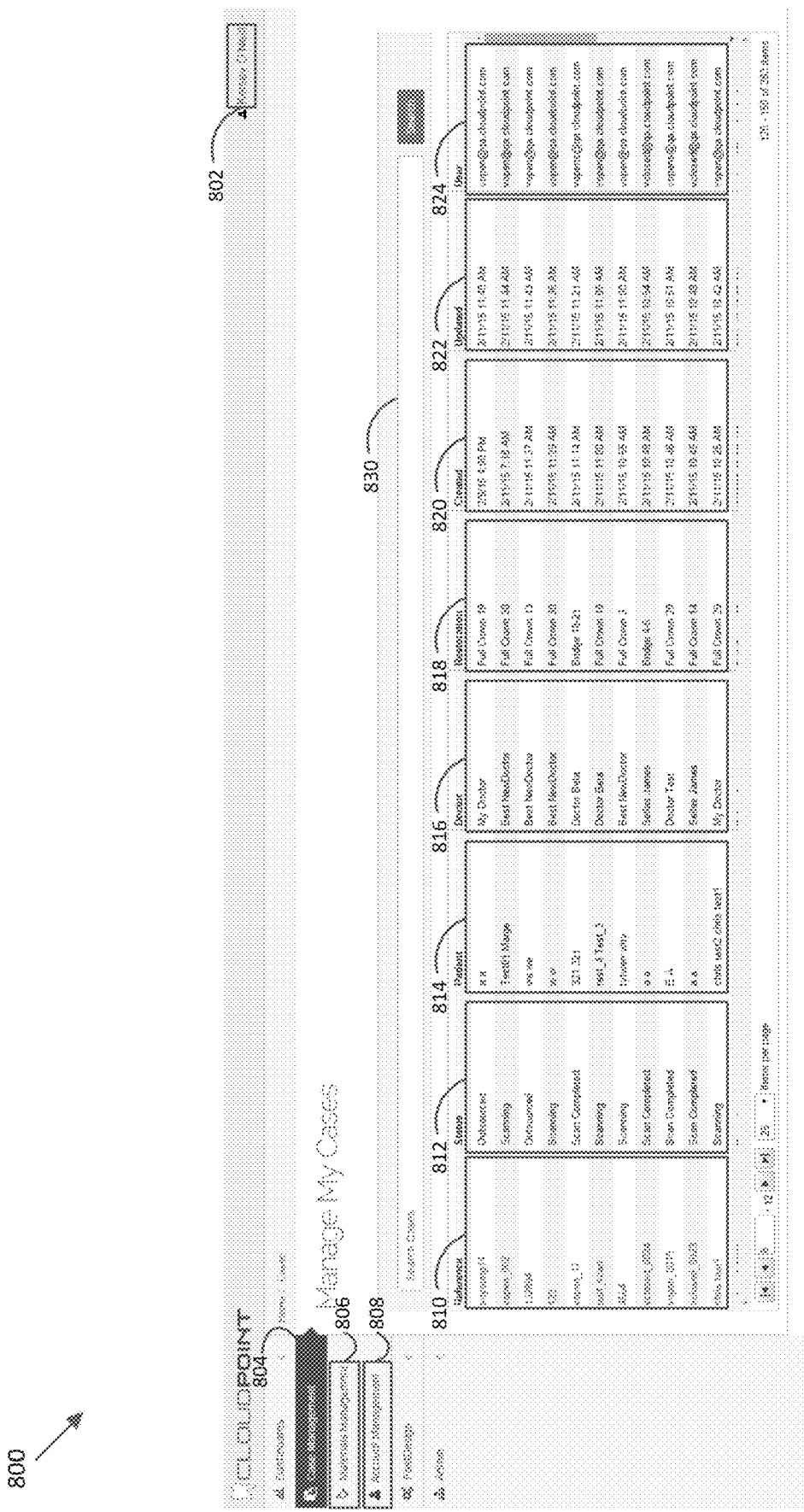
FIG. 8 is a graphic representation of a user interface showing a main queue displayed on a design device or a client device according to one embodiment.

FIG. 8 is a graphic representation of a user interface 800 showing a main queue displayed on a design device 145 or a client device 107 according to one embodiment. FIG. 8 depicts an administrator user page 800 of an administrator account showing dental restoration cases in the main queue. In one embodiment, the administrator user page 800 is from the view of a cloud server administrator 147 logged in with a cloud server administrator account. In another embodiment, the administrator user page 800 is from the view of a design center administrator 147 logged in with a design administrator account. Element 802 is a graphic representation of a user name or identifier of the administrator account. Elements 804, 806, 808 are graphic representations of tabs clickable for the administrator 147 of the user account 802 to view and conduct case management, material management, account management, respectively. The administrator 147 of the user account 802 can click any of the tabs to shift between them and to conduct the case management, material management and account management correspondingly.

In the depicted embodiment of 800, the administrator 147 of user account 802 selects the case management tab and dental restoration cases in the main queue are displayed. Element 810 includes graphic representations for identifiers of the dental restoration cases in the main queue. Element 812 includes graphic representations of status of the dental restoration cases in the main queue. For example, the status of the cases in the main queue can include, but not be limited to, scanning, scan completed, designing, design completed, fabricating, fabrication completed, outsourcing, etc. Other types of status of the cases known to those of skill in the art are also possible. Element 814 include graphic representations of patient information such as patient identifiers. For example, the patient information of each case may be provided by the client 175 (e.g., a doctor). Element 816 include graphic representations of the client (doctor) information such as doctor identifiers. Element 818 include graphic representations of restoration type information. For example, the restoration type can be a full crown or a bridge. Other dental restoration types known to those of skill in the art are also possible. As described above with reference to FIG. 2, the restoration type can be used to determine a design factor of the dental restoration design case. Element 820 include graphic representations of dates and times when the cases were created. Element 822 include graphic representations of dates and times when the cases were most recently updated. Element 824 include graphic representations of users 147 to whom the case has been assigned or routed. For example, the user 147 can be a user 147 for scanning the case. In another example, the user 147 can be a user 147 for designing or fabricating the case. The routing or assignment of the cases to users 147 can correspond to the status of the cases. Element 830 is a graphic representation of a search box that can be used by the administrator 802 to search a case in the main queue.

Figure 9:
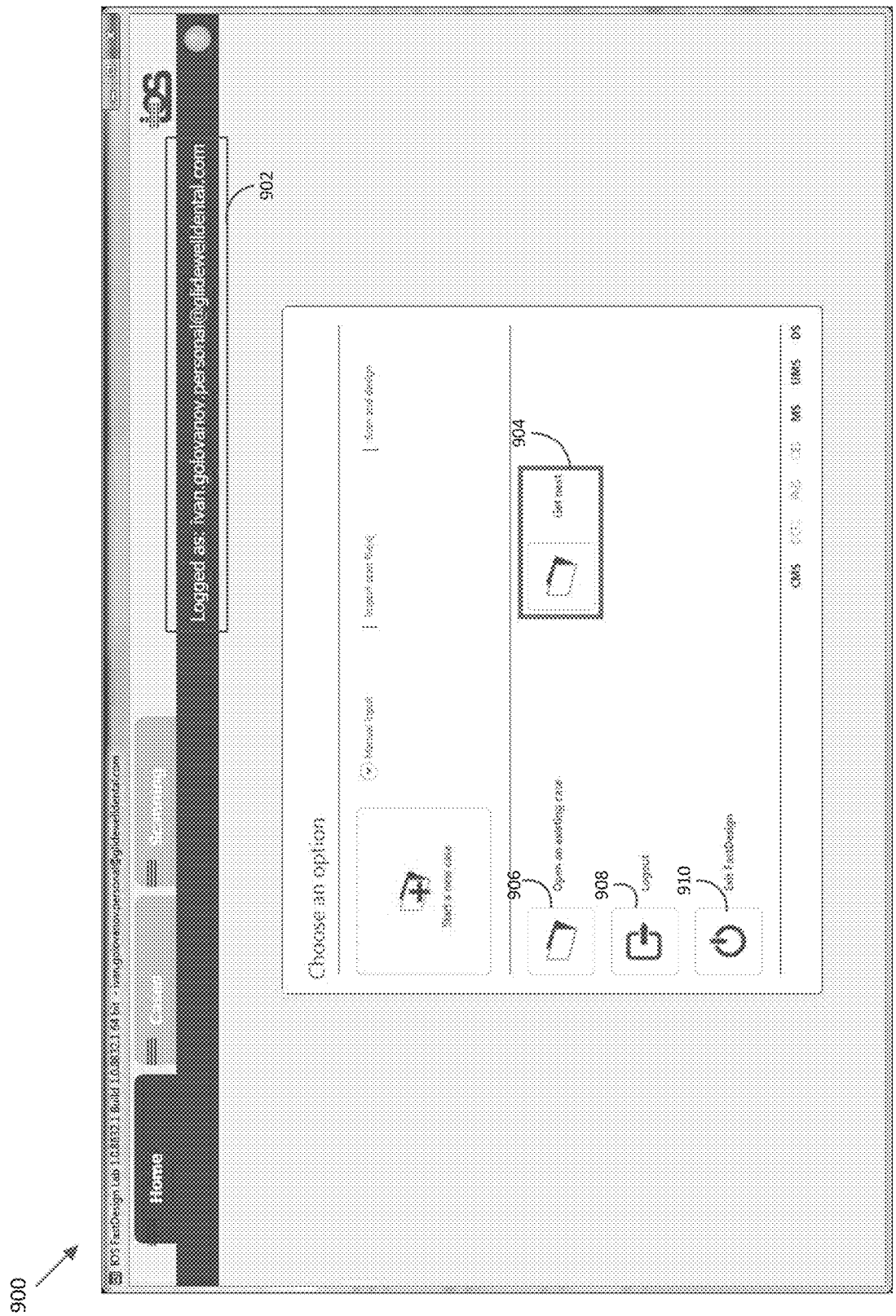
FIG. 9 is a graphic representation of a user interface showing a user home page of design software displayed on a design device or a client device according to one embodiment.

FIG. 9 is a graphic representation of a user interface 900 showing a user home page of the design software 149, 159 displayed on a design device 145, a client device 107 respectively, according to one embodiment. FIG. 9 depicts the user home page 900 for a user account of a user 147 (e.g., a design technician). Element 902 is a graphic representation of an email address as login information for the user account. Element 904 is a graphic representation of a "Get next" button that is clickable for the user 147 to request a next dental restoration design case. For example, the user 147 can click the button 904 to request a next dental restoration design case. As described above, responsive to the requesting, the queue module 123 may provide the next dental restoration design case in the user queue to the user 147. The queue module 123 may also determine a matching design case from the main queue and route the matching design case to the user queue. In one embodiment, the "Get next" button 904 may also provide queuing service for quality control workflow. For example, once a QC user 147 clicks the "Get next" button 904, the queue module 123 may determine a case for QC and route the case to the QC user 147.

In one embodiment, the "Get next" button 904 may also be a visual indicator on the status of the user's user queue. For example, the "Get next" button 904 indicates to the user 147 if a case in the user queue is available for design or not. For example, the "Get next" button 904 can be different colors or shades to indicate whether a case is available or not. In another embodiment, the "Get next" button 904 may also be a visual indicator on the status of the main queue. For example, the "Get next" button 904 can be different colors or shades to indicate different status of the main queue. The "Get next" button 904 can be red to indicate that the number of the cases in the user queue is less than a threshold, e.g., zero, one, five, 10, 20, etc. The "Get next" button 904 can be green to indicate that the number of cases in the user queue is above the threshold.

Element 906 is a graphic representation of a button clickable for the user 147 to open an existing case. Element 908 is a graphic representation of a button clickable for the user 147 to log out of the user account. Element 910 is a graphic representation of a button clickable for the user 147 to exit the design software 149, 159.

Figure 10:
FIG. 10 is a graphic representation of a user interface used by a quality control (QC) user displayed on a design device according to one embodiment.

FIG. 10 is a graphic representation of a user interface 1000 used by a quality control (QC) user 147 displayed on a design device 145 according to one embodiment. Element 1002 is a graphic representation of a dropdown menu showing a list of pre-defined rejection reasons. Each of the pre-defined rejection reasons in the dropdown menu 1002 can be selected by the QC user 147 if the QC user 147 tests the design of the case and decides there is such an error or issue of the design. Elements 1004a, 1004b are graphic representations of comments or texts specifying the rejection reasons. Elements 1006a, 1006b are arrows or lines connecting the comments or text to the place on the design where the QC user 147 decides the design errors or issues are.

In one embodiment, the dropdown menu 1002 enables the QC user 147 to select the rejection reasons from it. Once the QC user 147 selects a rejection reason, the user interface 1000 shows a text box 1004a, 1004b specifying the selected rejection reason. The user interface 1000 also allows the QC user 147 to further draw a line or arrow 1006a, 1006b to indicate where the error or issue specified by the rejection reason is on the design. Element 1008 is a graphic representation of a button clickable for the QC user 147 to reject the design of the case. For example, after having annotated the design with rejection reasons using the menu 1002 and text boxes 1004a, 1004b, the QC user 147 can click the rejection button 1008 to submit the rejection and the annotated design.

In one embodiment, when the annotated design is routed back to a design user 147, the text boxes 1004a, 1004b are also clickable for the design user 147 to view the error or issue specified by the text boxes 1004a, 1004b in the perspective of the QC user 147 while the QC user 147 placed the text boxes 1004a, 1004b. For example, when the design user 147 clicks on the text box 1004a, the portion of the dental restoration having an error specified by the text boxes 1004a can be shown in a precise and detailed view that is the same view of the QC user 147 when the QC user 147 checked out the error and placed the text box 1004a specifying the error there. The text box 1004b may have the similar function as text box 1004a. This functionality of being able to present a picture from a precise view of the QC user 147 to a design user 147 can reduce the ambiguity in the communication between the QC user 147 and the design user 147.

In one embodiment, the text boxes 1004a, 1004b may be used to automate simple design modifications without returning the annotated design to the design user 147 to fix the problem. For example, during the quality control text stage, the QC user 147 can use the text boxes 1004a, 1004b as tools to fix simple design errors or issues automatically. In addition, in one embodiment, the text boxes 1004a, 1004b may be used to communicate analytical data based upon a particular customer preference.

The above description is included to illustrate the operation of the preferred embodiments and is not meant to limit the scope of the invention. The scope of the invention is to be limited only by the following claims. From the above discussion, many variations will be apparent to one skilled in the relevant art that would yet be encompassed by the spirit and scope of the invention.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats. Furthermore, as will be apparent to one of ordinary skill in the relevant art, the modules, routines, features, attributes, methodologies and other aspects of the present invention can be implemented as software, hardware, firmware or any combination of the three. Also, wherever a component, an example of which is a module, of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

What is claimed is:

1. A computer-implemented method of fabricating a dental restoration design case, the method comprising:
    receiving one or more new dental restoration design cases, each of the one or more new dental restoration design cases associated with metadata describing at least one requirement related to dental restoration design;
    parsing the metadata to identify at least one design factor indicating the at least one requirement for each of the one or more new dental restoration design cases;
    storing the one or more new dental restoration design cases in a main queue;
    retrieving attribute data associated with one or more user accounts from a database;
    evaluating the at least one design factor of the one or more new dental restoration design cases in the main queue with the attribute data of one or more user accounts;
    ranking one or more matches between the at least one design factor and the attribute data associated with the one or more user accounts;
    routing a dental restoration design case to a user queue associated with a user account based on a ranking;
    responsive to determining that the dental restoration design case in the user queue has been designed by a design user, routing a designed case to a quality control (QC) queue for a QC user;
    detecting that the QC user has rejected the designed case;

receiving an annotated design of the designed case specifying an error associated with the design;
detecting whether the design user is available; and
returning the annotated design of the case to the user queue for the user account and placing the rejected design case on top of all other cases in the user queue if the design user is available, otherwise returning the annotated design of the case to the main queue; and
responsive to determining a dental restoration design case design is completed, fabricating the dental restoration design case.

2. The method of claim 1, wherein the attribute data comprises one or more from a group consisting of seniority level, skill level, and role.

3. The method of claim 1, wherein the ranking is based on how closely the dental restoration design case matches the attribute data of the user account.

4. The method of claim 3, wherein the routing comprises routing the dental restoration design case to the user queue associated with the user account with a highest match.

5. The method of claim 1, further comprising determining a role of a user based on the attribute data of the user account.

6. The method of claim 1, wherein the at least one design factor is specified by a client.

7. The method of claim 1, further comprising categorizing the dental restoration design case based on dental restoration types.

8. The method of claim 1, further comprising:
validating the one or more new dental restoration design cases based on the metadata;
wherein the step of parsing is based on validation of the one or more new dental restoration design cases.

9. The method of claim 1, further comprising:
receiving a request for a next dental restoration design case from the user account;
wherein the steps of the retrieving, the evaluating and the routing are responsive to receiving the request for the next dental restoration design case from a user account.

10. The method of claim 1, further comprising:
filtering a dental restoration design case based on its at least one design factor to determine whether the dental restoration design case is qualified for pre-processing; and
responsive to determining that a dental restoration design case is qualified for pre-processing, pre-processing the dental restoration design case to provide a dental restoration design proposal.

11. The method of claim 1, further comprising:
monitoring the number of the dental restoration design cases in the user queue associated with the user account of the design user;
detecting whether the number of the dental restoration design cases is below a threshold; and
indicating to the user account that the number of the dental restoration design cases is below the threshold.

12. The method of claim 1, further comprising:
monitoring the user account's status;
detecting whether an event has occurred based on the user account's status; and
responsive to detecting that the event has occurred, returning the dental restoration design case in the user queue associated with the user account to the main queue.

13. A computer-implemented method of fabricating a dental restoration design case, the method comprising:
receiving one or more new dental restoration design cases, each of the one or more new dental restoration design cases associated with metadata describing at least one requirement related to dental restoration design;
parsing the metadata to identify at least one design factor indicating the at least one requirement for each of the one or more new dental restoration design case;
storing the one or more new dental restoration design cases in a main queue;
receiving login information from a device operated by a design user;
identifying a user account for the design user based on the login information;
retrieving attribute data associated with the user account from a database, the attribute data describing a design skill level of the design user;
evaluating the at least one design factor of the one or more new dental restoration design cases in the main queue based on the attribute data of the user account to determine a dental restoration design case in the main queue that satisfies the attribute data of the user account;
routing the dental restoration design case to a user queue associated with the user account;
responsive to determining that the dental restoration design case in the user queue has been designed by the design user, routing the designed case to a quality control (QC) queue for a QC user;
detecting that the QC user has rejected the designed case;
receiving an annotated design of the designed case specifying an error associated with the design;
detecting whether the design user is available;
returning the annotated design of the designed case to the user queue for the user account and placing the rejected design case on top of all other cases in the user queue if the design user is available, otherwise returning the annotated design of the case to the main queue; and
responsive to determining a dental restoration design case design is completed, fabricating the dental restoration design case.

14. The method of claim 13, further comprising:
filtering the dental restoration design case based on its at least one design factor to determine whether the determined dental restoration design case is qualified for pre-processing; and
responsive to determining that the dental restoration design case is qualified for pre-processing, pre-processing the determined dental restoration design case to provide a dental restoration design proposal.

15. A system for fabricating a dental restoration design case, the system comprising:
a processor;
a non-transitory computer-readable storage medium comprising instructions executable by the processor to perform steps comprising:
receiving one or more new dental restoration design cases, each of the one or more new dental restoration design cases associated with metadata describing at least one requirement related to dental restoration design;
parsing the metadata to identify at least one design factor indicating the at least one requirement for each of the one or more new dental restoration design cases;
storing the one or more new dental restoration design cases in a main queue;
retrieving attribute data associated with one or more user accounts from a database;

evaluating the at least one design factor of the one or more new dental restoration design cases in the main queue with the attribute data of one or more user accounts;

routing the dental restoration design case to a user queue associated with a user account based on a ranking of matches between the at least one design factor and the attribute data associated with the one or more user accounts;

responsive to determining that the dental restoration design case in the user queue has been designed by a design user, routing a designed case to a quality control (QC) queue for a QC user;

detecting that the QC user has rejected the designed case;

receiving an annotated design of the designed case specifying an error associated with the design;

detecting whether the design user is available; and returning the annotated design of the case to the user queue for the user account and placing the rejected design case on top of all other cases in the user queue if the design user is available, otherwise returning the annotated design of the case to the main queue; and responsive to determining a dental restoration design case design is completed, fabricating the dental restoration design case.

16. The system of claim 15, wherein the attribute data comprises one or more from a group consisting of seniority level, skill level, and role.

17. The system of claim 15, wherein the ranking is based on how closely the dental restoration design case matches the attribute data of the account.

18. The system of claim 17, wherein the routing comprises routing the restoration design case to the user queue associated with a user account with a highest match.

19. The system of claim 18, further comprising determining a role of a user based on the attribute data of the account.

* * * * *